(12) United States Patent
Choi et al.

(10) Patent No.: US 11,591,630 B2
(45) Date of Patent: Feb. 28, 2023

(54) PEPTIDE FOR ENHANCING EXPRESSION EFFICIENCY OF TARGET PROTEIN, AND FUSION PROTEIN COMPRISING SAME

(71) Applicant: INTHERA INC., Seongnam-si (KR)

(72) Inventors: Deog Young Choi, Seoul (KR); Baik Lin Seong, Seoul (KR)

(73) Assignee: Inthera, Inc., Seongnam-si (KR)

( * ) Notice: Subject to any disclaimer, the term of this patent is extended or adjusted under 35 U.S.C. 154(b) by 0 days.

(21) Appl. No.: 16/766,651

(22) PCT Filed: Nov. 23, 2018

(86) PCT No.: PCT/KR2018/014495
§ 371 (c)(1),
(2) Date: May 22, 2020

(87) PCT Pub. No.: WO2019/103512
PCT Pub. Date: May 31, 2019

(65) Prior Publication Data
US 2022/0042063 A1 Feb. 10, 2022

(30) Foreign Application Priority Data

Nov. 23, 2017 (KR) .................. 10-2017-0157348
Nov. 22, 2018 (KR) .................. 10-2018-0145450

(51) Int. Cl.
| | | |
|---|---|---|
| C12P 21/02 | (2006.01) | |
| C07K 14/47 | (2006.01) | |
| C12N 9/06 | (2006.01) | |
| C12N 15/62 | (2006.01) | |

(52) U.S. Cl.
CPC .............. *C12P 21/02* (2013.01); *C07K 14/47* (2013.01); *C12N 9/0048* (2013.01); *C12N 15/62* (2013.01); *C07K 2319/21* (2013.01); *C07K 2319/35* (2013.01); *C07K 2319/50* (2013.01)

(58) Field of Classification Search
None
See application file for complete search history.

(56) References Cited

FOREIGN PATENT DOCUMENTS

| KR | 10-2004-0016654 A | 2/2004 |
| KR | 10-2013-0020206 A | 2/2013 |
| KR | 10-2013-0020208 A | 2/2013 |
| KR | 10-2017-0108880 A | 9/2017 |

OTHER PUBLICATIONS

Lim et al., "Site-specific albumination of a therapeutic protein with multi-subunit to prolong activity in vivo", Journal of Controlled Release, vol. 207, pp. 93-100, (Year: 2015).*
Oestreicher and Scazzocchio, "Sequence, Regulation, and Mutational Analysis of the Gene Encoding Urate Oxidase in Aspergillus nidulans", The Journal of Biological Chemistry, vol. 268, No. 31, pp. 23382-23389 (Year: 1993).*
International Search Report of corresponding PCT Application No. PCT/KR2018-014495—4 pages (May 27, 2019).
Oestreicher et al., "Sequence, Regulation, and Mutational Analysis of the Gene Encoding Urate Oxidase in Aspergillus nidulans*", The Journal of Biological Chemistry, vol. 268, No. 31—8 pages (Nov. 5, 1993).
Choi et al., "Protein Solubility and Folding Enhancement by Interaction with RNA", PLoS One, vol. 3, No. 7, E2677—11 pages (Jul. 16, 2008).
Francin et al., "The N-terminal Domain of Mammalian Lysyl-tRNA Synthetase Is a Functional tRNA-binding Domain*", The Journal of Biological Chemistry, vol. 277, No. 3—9 pages (Jan. 18, 2002).

* cited by examiner

*Primary Examiner* — Anand U Desai
(74) *Attorney, Agent, or Firm* — Knobbe, Martens, Olson & Bear, LLP

(57) ABSTRACT

The present invention relates to a novel peptide or a partial sequence thereof for enhancing expression efficiency of a target protein, and a fusion protein comprising the same. The novel peptide according to the present invention can enhance expression efficiency of a target protein, and furthermore, the peptide can also be applied to a solubility-enhancing fusion protein in order to enhance solubility of the target protein, so that solubility as well as expression efficiency of the target protein is enhanced, which allows such a peptide to be usefully used for production of a recombinant target protein.

8 Claims, 22 Drawing Sheets

Specification includes a Sequence Listing.

Fig 1
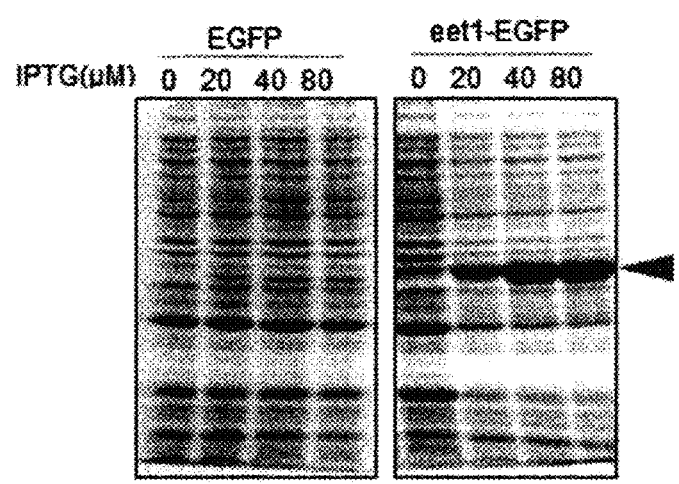
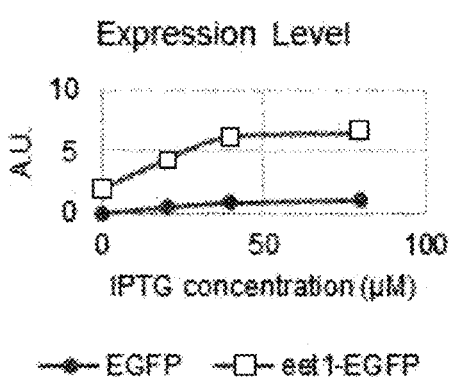
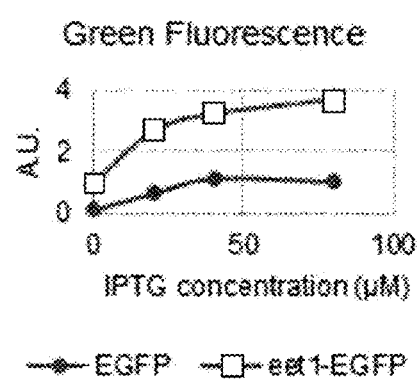

Fig 3
A
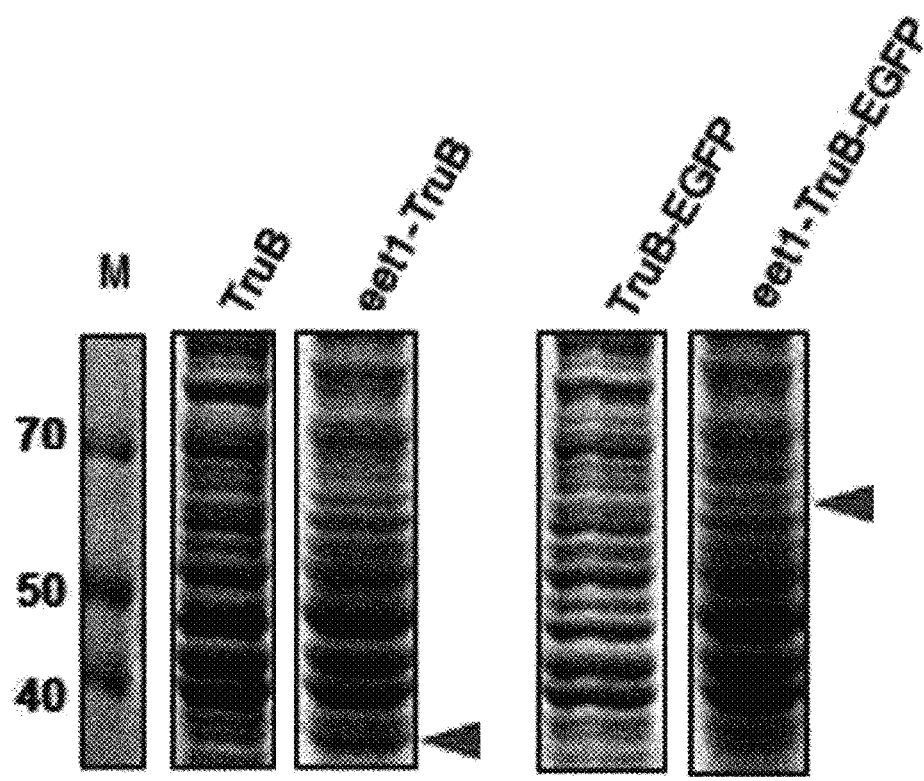
B
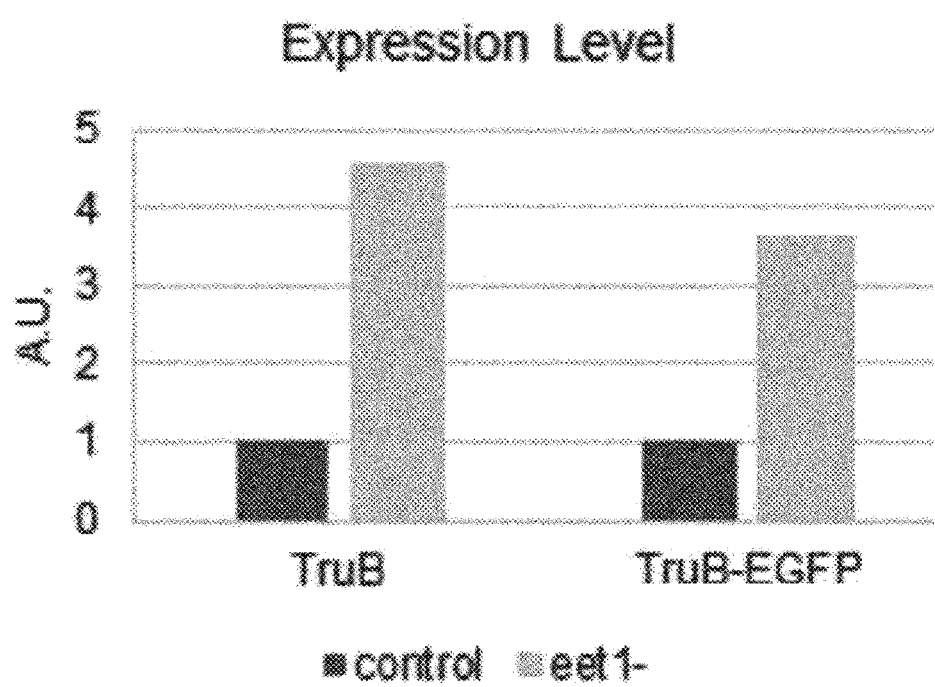

Fig 4
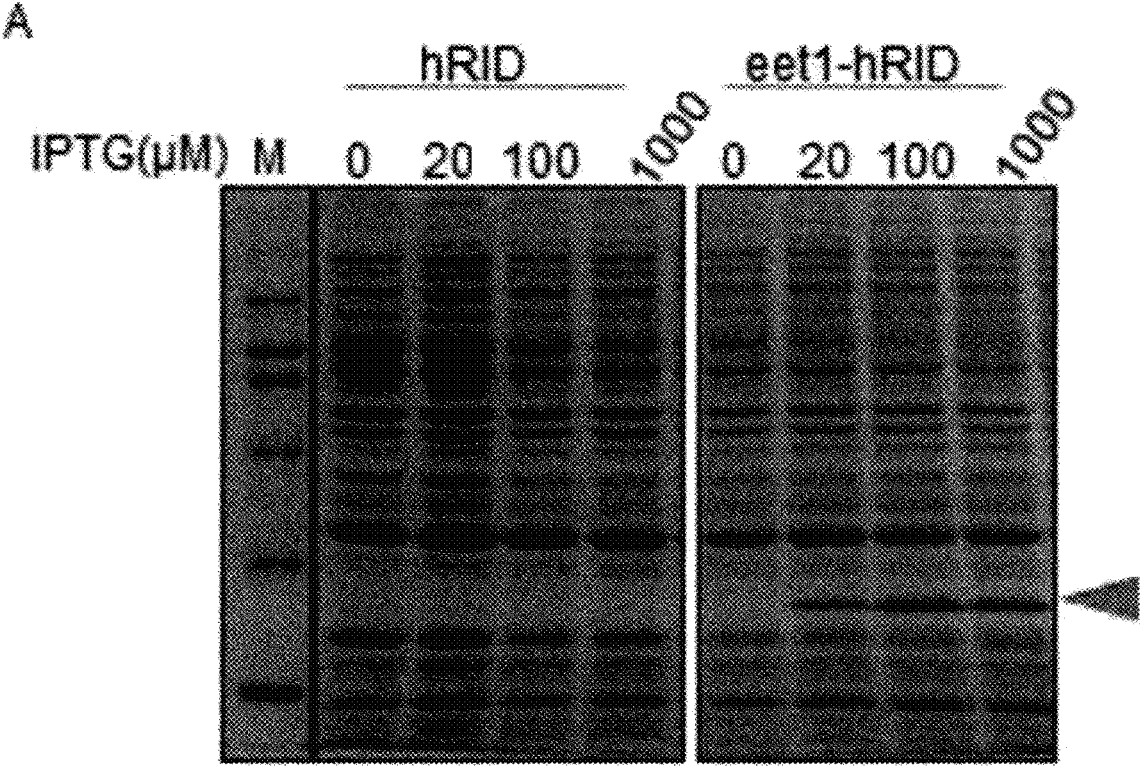
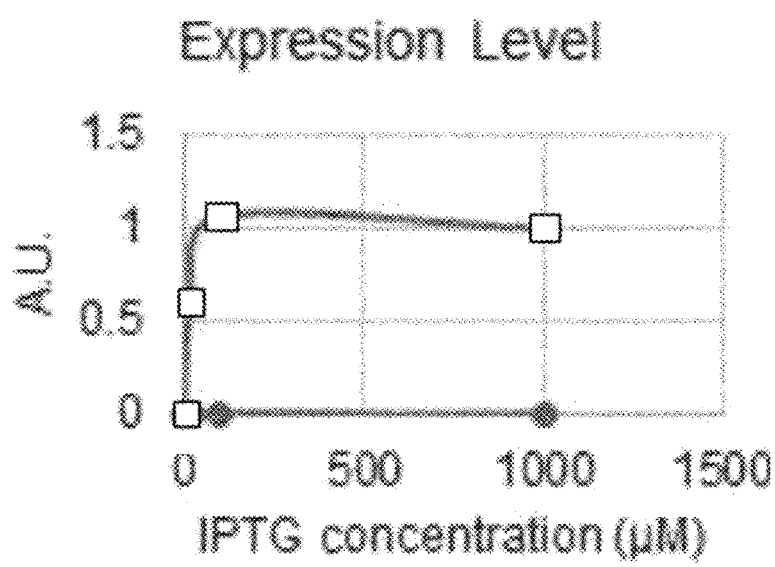

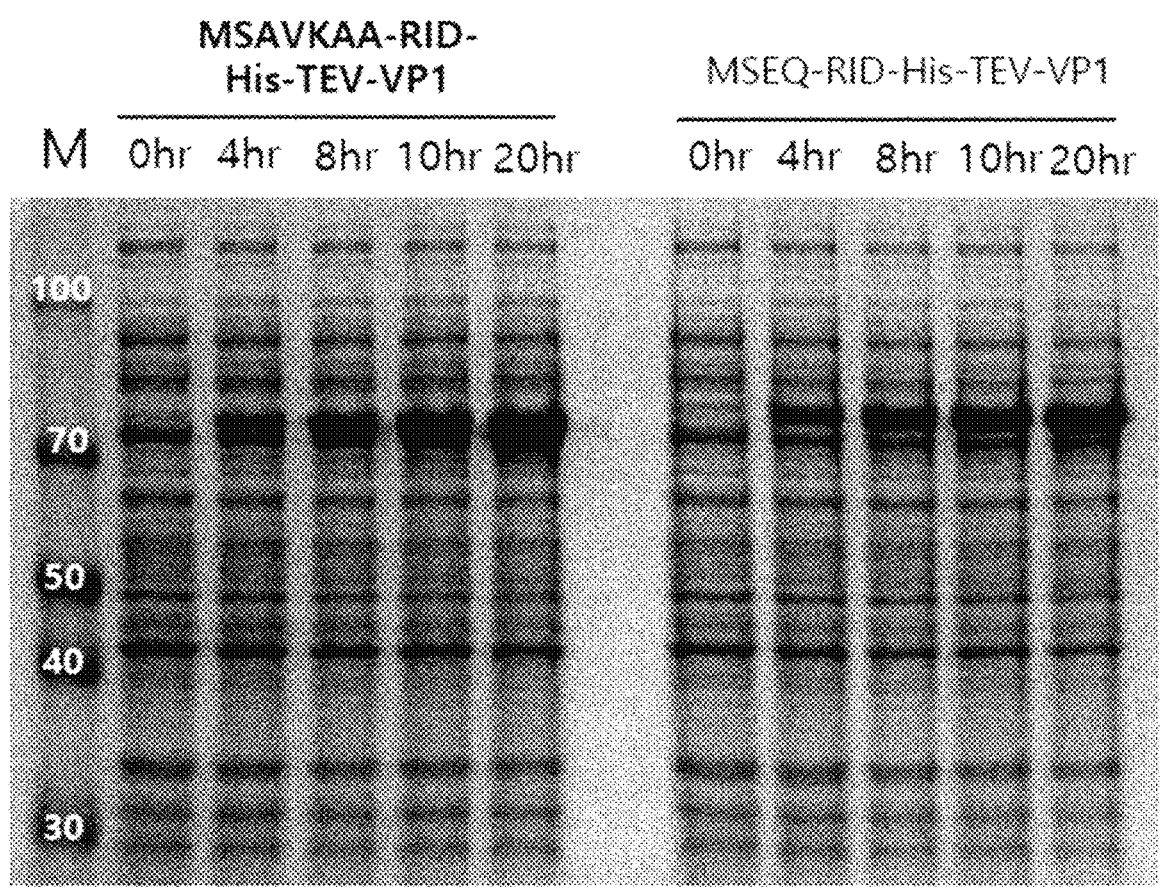

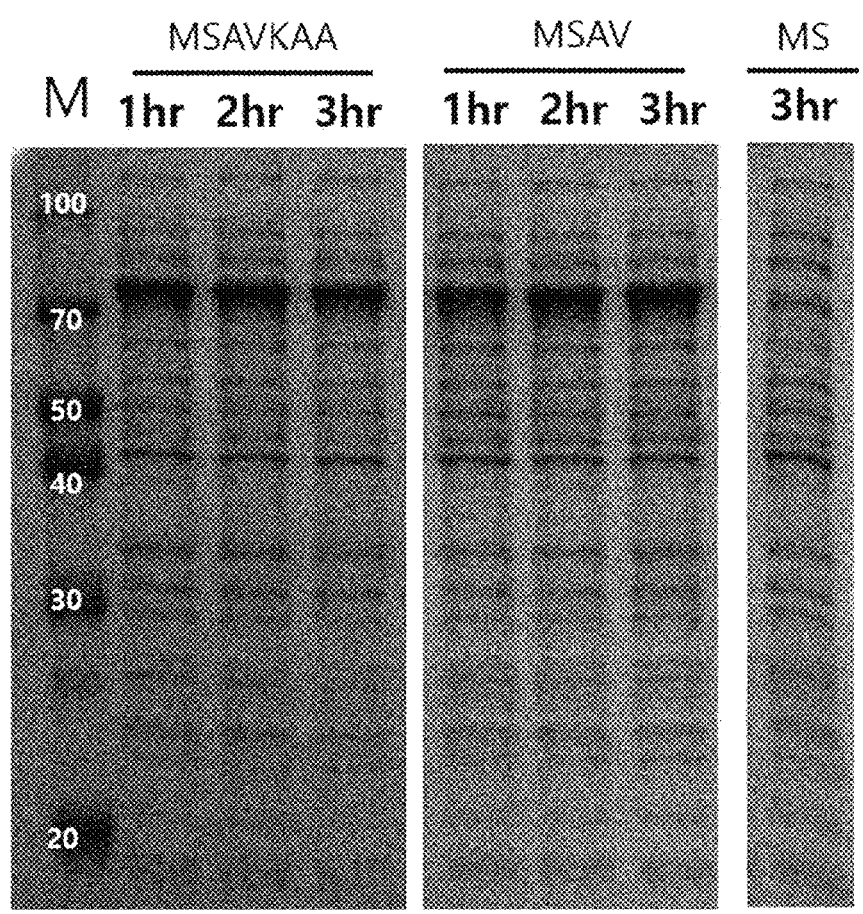

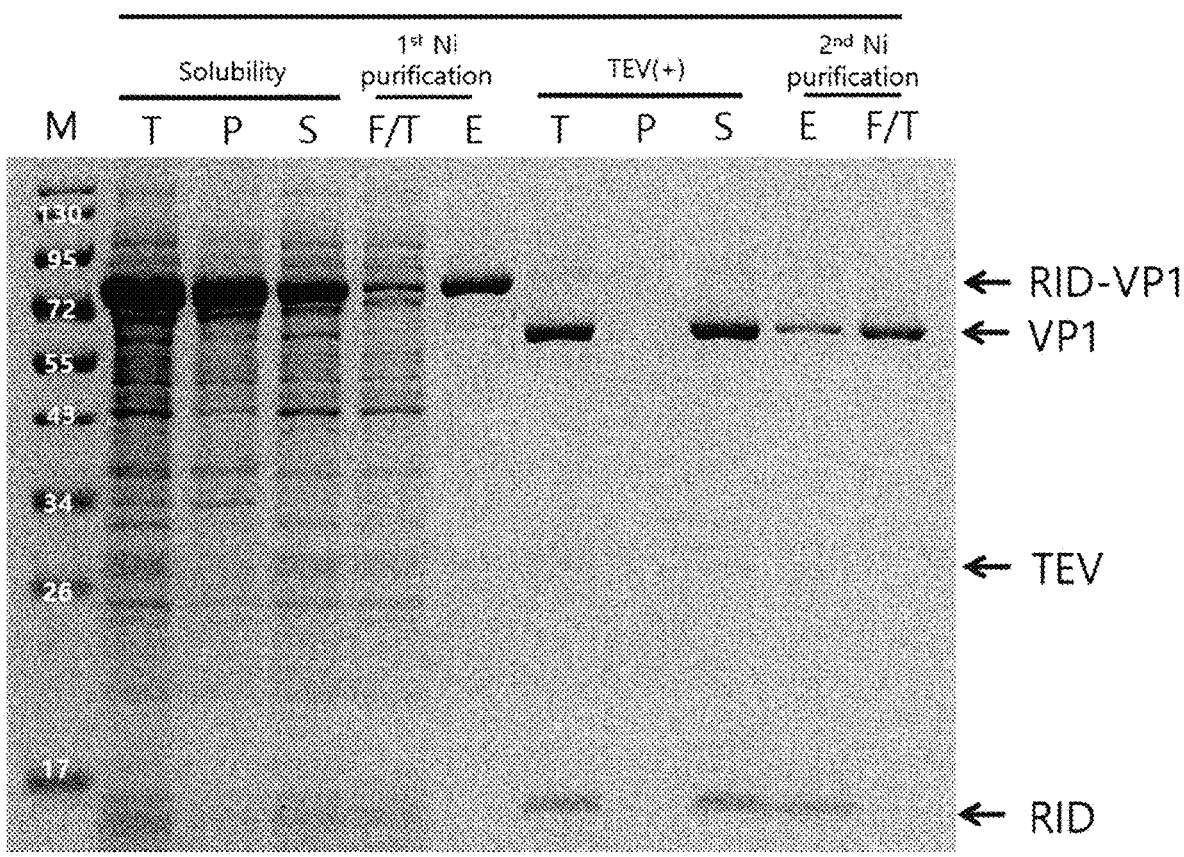

FIG. 11b

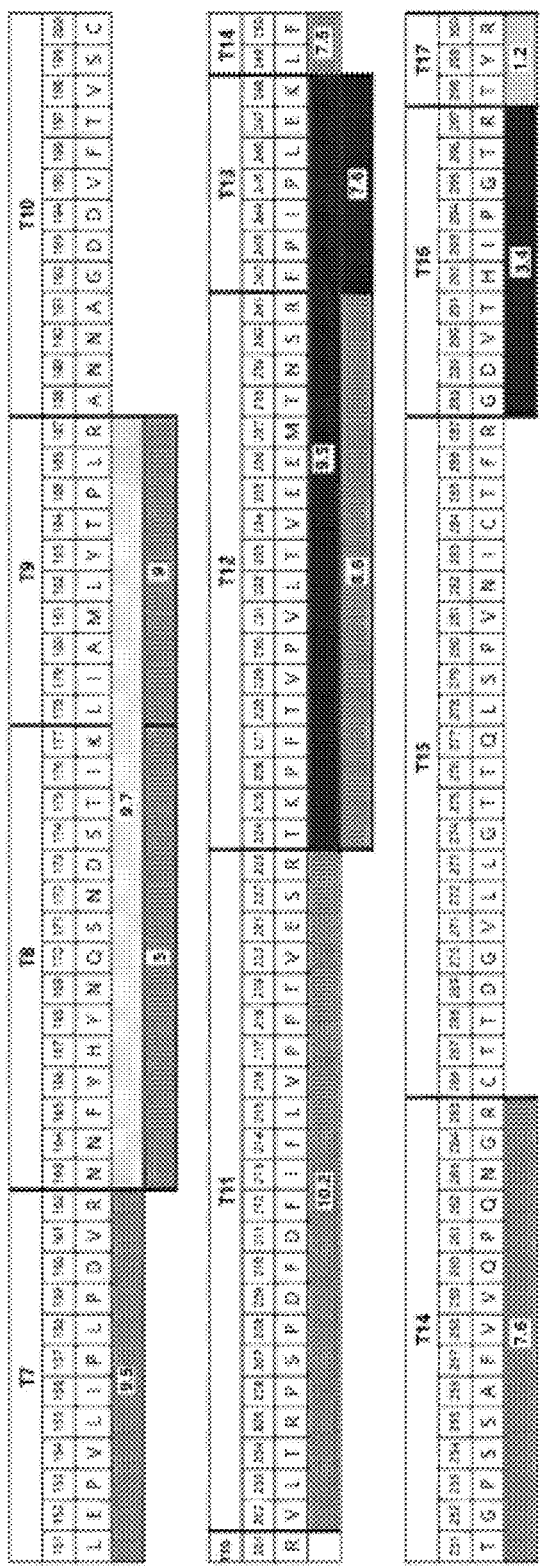
FIG. 11b-a

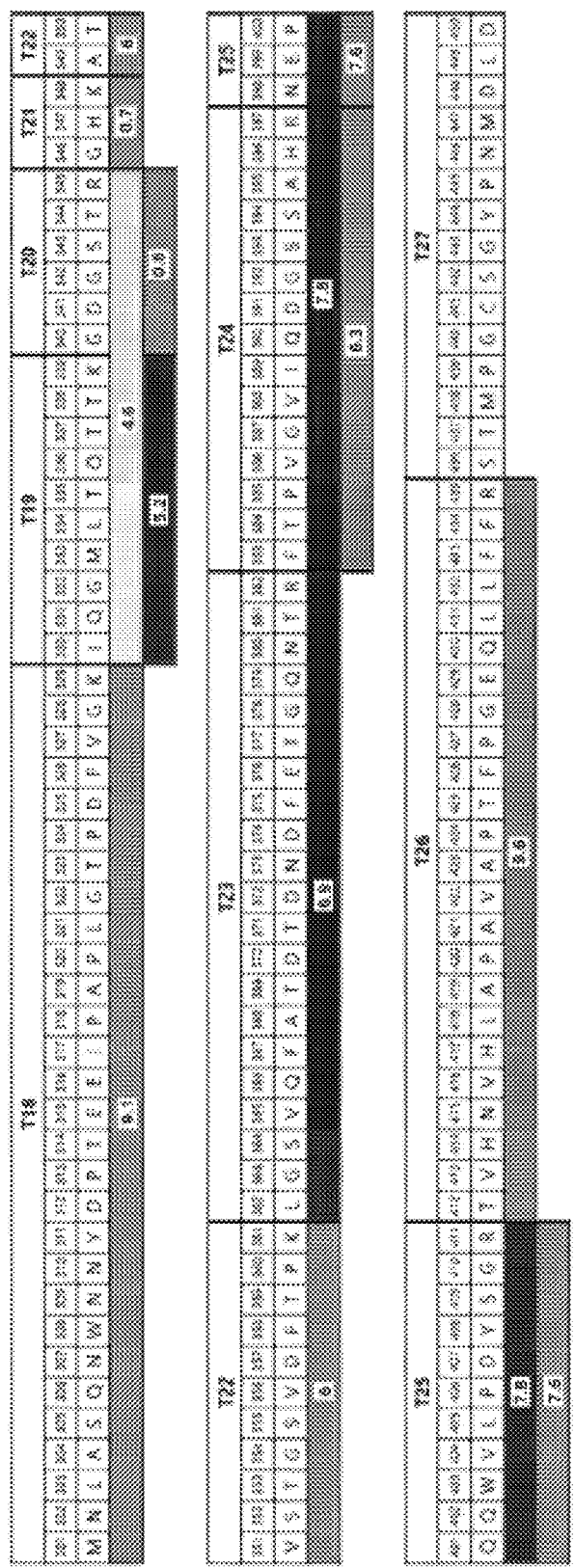
FIG. 11b-b

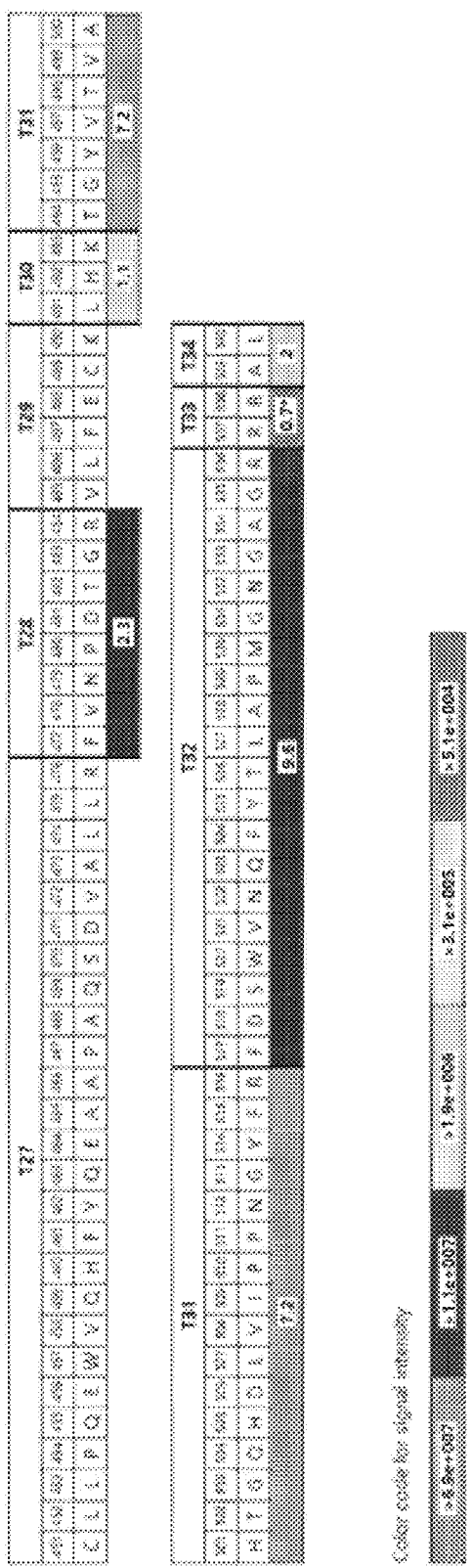
FIG. 11b-c

PEPTIDE FOR ENHANCING EXPRESSION EFFICIENCY OF TARGET PROTEIN, AND FUSION PROTEIN COMPRISING SAME

REFERENCE TO SEQUENCE LISTING

The present application is being filed along with a Sequence Listing in electronic format. The Sequence Listing is provided as a file entitled 56287756_1.TXT, created and last modified on Oct. 12, 2022, which is 25.3 Kb in size. The information in the electronic format of the Sequence Listing is incorporated herein by reference in its entirety.

TECHNICAL FIELD

The present invention relates to a novel peptide for enhancing expression efficiency of a target protein, and a fusion protein comprising the same. More specifically, the present invention relates to a peptide consisting of 7 amino acids derived from urate oxidase or a peptide containing a part thereof, and to a fusion protein comprising the peptide and RNA interacting domain (RID) as a fusion partner thereof.

BACKGROUND ART

The key to modern biotechnology is production of recombinant proteins; and in particular, it is important to produce large amounts of recombinant proteins. Recombinant proteins produced in large amounts are very important for production and recovery of active exogenous proteins, crystallization for functional studies, industrialization, and the like. To date, many recombinant protein production studies using *E. coli* have been conducted, because *E. coli* has advantages of easy manipulation, short growth time, safe expression, low cost, and easy scalability. However, since exogenous recombinant proteins produced in *E. coli* have low expression levels or lack adequate "post-translational chaperons" or "post-translational processing," a disadvantage that the produced recombinant proteins result in formation of insoluble protein inclusion bodies has been pointed out (Francois Baneyx, Recombinant protein expression in *Escherichia coli*, *Current Opinion in Biotechnology* (1999), 10:411-421).

The problem that proteins are produced in insoluble form has been addressed by developing a method in which the protein is fused with a highly-soluble protein and the resulting fusion protein is expressed (Dominic Esposito and Deb K Chatterjee, Enhancement of soluble protein expression through the use of fusion tags, *Current Opinion in Biotechnology* (2006), 17:353-358). In addition, attempts have been made to increase solubility of recombinant proteins using an RNA binding domain such as lysyl tRNA synthetase (LysRS) (Choi, S. I. et al., Protein solubility and folding enhancement by interaction with RNA, *PLoS ONE* (2008), 3:e2677). However, LysRS is not only a large protein of more than about 100 kDa (its monomer size=about 58 kDa), but also has steric hindrance due to its structural limitation of having to form a dimer; and therefore, LysRS may prevent a recombinant protein from forming a three-dimensional structure or forming a dimer or higher-order multimer, or from being converted into monomers, so that the recombinant protein does not have a desired active form. Thus, RNA interacting domain (RID) (N-terminal appended RNA binding domain of lysyl tRNA synthetase) has been used as an RNA binding domain for replacing LysRS. However, RID itself has a great drawback of having a very low expression level.

Meanwhile, norovirus is one of the major pathogens causing acute gastroenteritis worldwide, with 200,000 children of developing countries under the age of 5 dying from norovirus every year. Norovirus is mainly transmitted through the fecal-oral route and causes nausea, vomiting, diarrhea, dehydration, and the like. Norovirus, a member of the Caliciviridae family, is a non-enveloped virus and is about 30 to 40 nm in diameter. This virus consists of single-stranded (+)RNA having a length of 7.6 kbp, and has three open reading frames (ORFs). Among these, ORF2 encodes the major structural protein VP1 that constitutes norovirus; and ORF3 encodes the protein VP2 that is not directly involved in structural formation thereof. VP1 has a total size of 59 kDa and forms a dimer. As such, 90 dimers result from self-assembly of VP1s, in which a total of 180 VP1s form one viral particle. The VP1 protein consists of two domains, S domain and P domain. The S domain acts to form a structure of the protein, and the P domain is involved in inducing an actual immune response.

To date, no cell culture method for norovirus is known and no suitable animal model has been developed. Therefore, in order to develop an effective norovirus vaccine, it is essential to develop a vaccine in the form of virus-like particles (VLPs) on which no limitation is imposed in terms of cell culture. VLPs are highly complex and sophisticated structures obtained by allowing viral structural proteins to be specifically expressed to exhibit a structure similar in appearance to the wild-type virus. Because of their similar structure to the wild-type virus, VLPs have advantages capable of inducing a high-level immune response in the body and stimulating both T-cell and B-cell immune pathways. In addition, VLPs are characterized by having no infectious capacity due to absence of genetic material in their formed structure, and thus being highly safe, and by showing excellent structural stability. However, VLPs have a disadvantage that due to their complex structure, it is very difficult to create complete VLPs.

It is known that norovirus VLPs can be produced in baculovirus-insect cells and can also be produced in yeast. However, although there have been reports that a structural protein (VP1) is expressed in soluble form in *E. coli*, there has been no report that virus-like particles (VLPs) are formed in *E. coli*. From the viewpoint that most casualties caused by norovirus occur in developing countries, development of norovirus VLPs that are derived from *E. coli* will provide a low-cost vaccine as compared with vaccines obtained using other expression systems, and thus will be able to make a great contribution to human society.

In the previous study, the present inventors revealed that RNA binding domain (RBD)-containing lysyl tRNA synthetase (LysRS) as a binding partner is involved in protein folding and increased solubility of various proteins. However, LysRS is not only a large protein of more than about 100 kDa (its monomer size=about 58 kDa), but also has steric hindrance due to its structural limitation of having to form a dimer; and therefore, LysRS may prevent a recombinant protein from forming a three-dimensional structure or forming a dimer or higher-order multimer, or from being converted into monomers, so that the recombinant protein does not have a desired active form. Thus, RNA interacting domain (RID) (N-terminal appended RNA binding domain of lysyl tRNA synthetase) has been used as an RNA binding domain for replacing LysRS. However, RID itself has a great drawback of having a very low expression level.

Although a protein expression level may be determined by several factors, the N-terminal sequence, precisely the mRNA sequence, of a protein is known to be important for the protein expression level.

Accordingly, while studying solubility and expression efficiency of proteins, the present inventors have identified that the protein, urate oxidase, is abnormally well expressed in *E. coli*, and have identified effects of the N-terminal sequence of urate oxidase on expression level of a target protein and on expression of RID, thereby completing the present invention.

Technical Problem

The present invention intends to solve the above problems. The present inventors have identified that a peptide consisting of 7 amino acids derived from urate oxidase or a partial sequence thereof plays a crucial role in enhancing expression efficiency of a target protein, and the peptide consisting of 7 amino acids derived from urate oxidase is also applied to RNA interacting domain (RID) known as a solubility-enhancing partner, so that the target protein can have increased solubility as well as enhanced expression efficiency, thereby completing the present invention.

Accordingly, an object of the present invention is to provide a peptide containing 7 amino acids derived from urate oxidase or a partial sequence thereof; a polynucleotide encoding the peptide; an expression vector comprising the peptide; and a host cell transformed with the expression vector.

Another object of the present invention is to provide a fusion protein that comprises a peptide containing 7 amino acids derived from urate oxidase or a partial sequence thereof and RID as a fusion partner thereof; an expression vector comprising the fusion protein; and a host cell transformed with the expression vector.

Yet another object of the present invention is to provide a method for producing a soluble target protein, comprising the steps of: constructing an expression vector that contains a polynucleotide encoding a target protein and a polynucleotide which is linked to the 5'-end of the polynucleotide encoding the target protein and encodes a peptide that enhances expression efficiency of the target protein; introducing the expression vector into a host cell, to prepare a transformant; and culturing the transformant so that expression of a recombinant target protein is induced, and obtaining the recombinant target protein.

Still yet another object of the present invention is to provide a recombinant expression vector for producing a norovirus vaccine, the recombinant expression vector having norovirus VP1 protein as a target protein and being capable of not only enhancing solubility of the VP1 protein but also increasing expression efficiency of the VP1 protein, in which the VP1 protein is poorly expressed in prokaryotic cells; a host cell transformed with the vector; and a method for producing a norovirus vaccine using the vector and the host cell.

Solution to Problem

According to the first embodiment, the present invention intends to provide a peptide for enhancing expression efficiency of a target protein, the peptide comprising the amino acid sequence represented by SEQ ID NO: 1 or a partial sequence thereof.

As used herein, the term "urate oxidase" (EC 1.7.3.3 (uricase)) refers to an enzyme that acts on the purine degradation mechanism. Uricase is an enzyme that oxidizes uric acid to allantoin. In higher primates, including humans, uricase does not exist and uric acid is the end product of purine metabolism. The metabolites thereof, free acid and urate salt, are both insoluble in water, so they precipitate depending on individual differences and cause gout. In order to treat gout efficiently, a treatment, in which uricase that does not exist in humans is directly injected into a human, has been put to practical use.

As used herein, the term "target protein" refers to a protein that a person skilled in the art intends to produce in large amounts, and includes any protein that can be obtained by inserting a polynucleotide encoding the protein into a recombinant expression vector and causing the protein to be expressed in a host cell.

As used herein, the term "peptide for enhancing expression efficiency of a target protein" or "expression enhancer tag (eet)" refers to a short peptide sequence that is fused to the N-terminus of the target protein and expressed together therewith, thereby enhancing expression efficiency of the protein. Specifically, in the present invention, the peptide for enhancing expression efficiency of a target protein contains the 7-amino acid sequence represented by SEQ ID NO: 1 or a partial sequence thereof.

As used herein, the term "recombinant protein" or "fusion protein" refers to a protein obtained by linking another protein to or adding another amino acid sequence to the N-terminus or C-terminus of an original target protein sequence.

In the peptide for enhancing expression efficiency of a target protein according to the present invention, the amino acid sequence of SEQ ID NO: 1 or a partial sequence thereof may be derived from urate oxidase.

In addition, in the peptide for enhancing expression efficiency of a target protein according to the present invention, the partial sequence of SEQ ID NO: 1 may contain the amino acid sequence represented by SEQ ID NO: 2.

In the peptide for enhancing expression efficiency of a target protein according to the present invention, the peptide may bind to the N-terminus of the target protein.

In the peptide for enhancing expression efficiency of a target protein according to the present invention, the target protein may be at least one selected from the group consisting of antigens, antibodies, cell receptors, enzymes, structural proteins, serum, and cellular proteins.

In an embodiment of the present invention, the antigen may be norovirus-derived VP1 protein.

In addition, the present invention intends to provide a polynucleotide encoding the peptide for enhancing expression efficiency of a target protein.

In an embodiment of the present invention, the polynucleotide may be a polynucleotide encoding the amino acid sequence of SEQ ID NO: 1 or SEQ ID NO: 2.

In a preferred embodiment of the present invention, the polynucleotide encoding SEQ ID NO: 1 may be a sequence represented by SEQ ID NO: 3.

In a preferred embodiment of the present invention, the polynucleotide encoding SEQ ID NO: 2 may be a sequence represented by SEQ ID NO: 4.

In addition, the present invention intends to provide an expression vector comprising the peptide for enhancing expression efficiency of a target protein.

The present invention intends to provide an expression vector, comprising: a polynucleotide encoding a target protein; and a polynucleotide encoding a peptide for enhancing expression efficiency of the target protein, linked to the 5'-end of the polynucleotide encoding the target protein.

As used herein, the term "expression vector" refers to a linear or circular DNA molecule that consists of a fragment encoding a polypeptide of interest, operably linked to an additional fragment provided for transcription on the expression vector. Such an additional fragment includes a promoter and a stop codon sequence. The expression vector also contains at least one replication origin, at least one selection marker, a polyadenylation signal, and the like. The expression vector is generally derived from plasmid or viral DNA or contains both elements.

As used herein, the term "operably linked" refers to fragments arranged to function so that transcription initiates from a promoter and proceeds, via a coding sequence, to a stop codon.

In the expression vector according to the present invention, the expression vector may be a plasmid, a viral vector, a phage particle, or a genomic insert. The expression vector may be transformed into a host cell, and then replicated irrespective of the genome of the host cell or integrated into the genome of the host cell.

In addition, the present invention intends to provide a host cell transformed with the expression vector containing the peptide for enhancing expression efficiency of a target protein.

As used herein, the term "transformation" or "introduction" refers to introducing DNA into a host so that DNA is replicable as an extrachromosomal element or by chromosomal integration completion. Examples of the method of performing transformation with the expression vector according to the present invention include, but are not limited to, electroporation, calcium phosphate (CaPO$_4$) method, calcium chloride (CaCl$_2$) method, microinjection, polyethylene glycol (PEG) method, DEAE-dextran method, cationic liposome method, or lithium acetate-DMSO method.

In the host cell according to the present invention, the host cell is preferably a host cell having high DNA introduction efficiency and high expression efficiency of introduced DNA, and any microorganism including prokaryotes and eukaryotes may be used. Preferably, the host cell may be *E. coli*.

In addition, the present invention intends to provide a method for producing a target protein with enhanced expression efficiency. The method for producing a target protein may comprise the steps of:

(A) constructing an expression vector that contains a recombinant target protein in which a peptide containing the amino acid sequence of SEQ ID NO: 1 or a partial sequence thereof is linked to the N-terminus of the target protein;

(B) introducing the expression vector into a host cell; and (C) producing the recombinant target protein from the host cell.

According to the second embodiment, the present invention intends to provide a fusion protein for enhancing expression efficiency and solubility of a target protein, the fusion protein comprising: a peptide containing the amino acid sequence of SEQ ID NO: 1 or a partial sequence thereof; and RNA interacting domain (RID) as a fusion partner thereof.

As used herein, the term "RID", "RNA interacting domain", "N terminal appended RNA binding domain of lysyl tRNA synthetase", or "LysRS RNA interacting domain" refers to a unique N-terminal extension site of LysRS involved in interaction between RNA and other proteins.

In the fusion protein for enhancing expression efficiency and solubility of a target protein according to the present invention, the amino acid sequence of SEQ ID NO: 1 may be derived from urate oxidase.

In the fusion protein for enhancing expression efficiency and solubility of a target protein according to the present invention, the peptide may bind to the N-terminus of the target protein.

In the fusion protein for enhancing expression efficiency and solubility of a target protein according to the present invention, RID may contain the amino acid sequence represented by SEQ ID NO: 7.

The fusion protein of the present invention may contain the amino acid sequence represented by SEQ ID NO: 9.

In the fusion protein for enhancing expression efficiency and solubility of a target protein according to the present invention, the target protein may be at least one selected from the group consisting of antigens, antibodies, cell receptors, enzymes, structural proteins, serum, and cellular proteins.

In addition, the present invention intends to provide an expression vector for enhancing expression efficiency and solubility of a target protein, the expression vector having a fusion protein that contains a peptide containing the amino acid sequence of SEQ ID NO: 1 or a partial sequence thereof, the peptide binding to the N-terminus of the target protein, and RID as a fusion partner thereof.

The expression vector of the present invention contains a polynucleotide encoding a target protein and a polynucleotide that is linked to the 5'-end of the polynucleotide encoding the target protein and encodes a fusion protein, in which the fusion protein may be a fusion protein of a peptide for enhancing expression efficiency of the target protein with RID.

In the expression vector according to the present invention, the expression vector may be a plasmid, a viral vector, a phage particle, or a genomic insert. The expression vector may be transformed into a host cell, and then replicated irrespective of the genome of the host cell or integrated into the genome of the host cell.

In addition, the present invention intends to provide a host cell transformed with an expression vector for enhancing expression efficiency and solubility of a target protein, the expression vector having a fusion protein that contains a peptide containing the amino acid sequence of SEQ ID NO: 1 or a partial sequence thereof, the peptide binding to the N-terminus of the target protein, and RID as a fusion partner thereof.

In the host cell according to the present invention, the host cell is preferably a host cell having high DNA introduction efficiency and high expression efficiency of introduced DNA, and any microorganism including prokaryotes and eukaryotes may be used. Preferably, the host cell may be *E. coli*.

In addition, the present invention intends to provide a method for producing a target protein with enhanced expression efficiency and solubility. The method for producing a target protein may comprise the steps of:

(A) constructing an expression vector that contains a recombinant target protein in which a fusion protein, which contains a peptide containing the amino acid sequence of SEQ ID NO: 1 or a partial sequence thereof and RID as a fusion partner thereof for increasing solubility of the target protein, is linked to the N-terminus of the target protein;

(B) introducing the expression vector into a host cell; and (C) producing the recombinant target protein from the host cell.

In addition, the present invention intends to provide a recombinant expression vector for production of norovirus vaccine, comprising a polynucleotide that encodes: norovirus-derived VP1 protein as a target protein; and a peptide for enhancing expression efficiency of the target protein, the peptide containing 7-amino acid sequence derived from urate oxidase or a partial sequence thereof.

In the recombinant expression vector for production of norovirus vaccine of the present invention, the amino acid sequence of SEQ ID NO: 1 or a partial sequence thereof in the peptide for enhancing expression efficiency of a target protein may be derived from urate oxidase.

In addition, in the peptide for enhancing expression efficiency of a target protein according to the present invention, the partial sequence of SEQ ID NO: 1 may include the amino acid sequence represented by SEQ ID NO: 2.

The recombinant expression vector for production of norovirus vaccine of the present invention may contain a polynucleotide encoding the peptide of SEQ ID NO: 1 for enhancing expression efficiency of a target protein.

In a preferred embodiment of the present invention, the polynucleotide encoding the peptide of SEQ ID NO: 1 may be a sequence represented by SEQ ID NO: 3.

In a preferred embodiment of the present invention, the polynucleotide encoding the peptide of SEQ ID NO: 2 may be a sequence represented by SEQ ID NO: 4.

In a preferred embodiment of the present invention, the recombinant expression vector for production of norovirus vaccine may further contain: a polynucleotide encoding 1 to 6 histidines; and a polynucleotide encoding a protease recognition site.

In the recombinant expression vector for production of norovirus vaccine of the present invention, the polynucleotide encoding 1 to 6 histidines may be represented by SEQ ID NO: 10.

In the recombinant expression vector for production of norovirus vaccine of the present invention, the protease may be TEV.

In the recombinant expression vector for production of norovirus vaccine of the present invention, the polynucleotide encoding a protease recognition site may be represented by SEQ ID NO: 11.

In the expression vector according to the present invention, the expression vector may be a plasmid, a viral vector, a phage particle, or a genomic insert. The expression vector may be transformed into a host cell, and then replicated irrespective of the genome of the host cell or integrated into the genome of the host cell.

In addition, the present invention intends to provide a host cell transformed with the expression vector that contains the norovirus-derived VP1 protein; and a peptide for enhancing expression efficiency of a target protein.

In the host cell according to the present invention, the host cell is preferably a host cell having high DNA introduction efficiency and high expression efficiency of introduced DNA, and any microorganism including prokaryotes and eukaryotes may be used. Preferably, the host cell may be *E. coli*.

In addition, the present invention intends to provide a method for producing a norovirus vaccine with enhanced expression efficiency. The method for producing a norovirus vaccine may comprise the steps of:

(a) producing a recombinant expression vector for production of norovirus vaccine, the recombinant expression vector containing a polynucleotide that encodes: norovirus-derived VP1 protein as a target protein; and a peptide for enhancing expression efficiency of the target protein, the peptide containing the amino acid sequence of SEQ ID NO: 1 or a partial sequence thereof;

(b) introducing the expression vector into a host cell, to produce a transformant; and (c) culturing the transformant so that expression of a recombinant fusion protein is induced, and obtaining the recombinant fusion protein.

In addition, the present invention intends to provide a recombinant expression vector for production of norovirus vaccine, comprising a polynucleotide that encodes: norovirus-derived VP1 protein as a target protein; and a fusion protein for enhancing expression efficiency and solubility of the target protein, the fusion protein containing a peptide, which contains the amino acid sequence of SEQ ID NO: 1 or a partial sequence thereof, and RID as a fusion partner of the peptide.

That is, the expression vector of the present invention contains a polynucleotide encoding a target protein and a polynucleotide that is linked to the 5'-end of the polynucleotide encoding the target protein and encodes a fusion protein, in which the fusion protein may be a fusion protein of a peptide for enhancing expression efficiency of the target protein with RID.

As used herein, the term "fusion protein" or "recombinant protein" refers to a protein obtained by linking another protein to or adding another amino acid sequence to the N-terminus or C-terminus of an original target protein sequence.

In addition, the present invention intends to provide a method for producing a norovirus vaccine with enhanced expression efficiency and solubility. The method for producing a norovirus vaccine may comprise the steps of:

(A) constructing an expression vector that contains a recombinant target protein in which a fusion protein, which contains a peptide containing the amino acid sequence of SEQ ID NO: 1 or a partial sequence thereof and RID as a fusion partner thereof for increasing solubility of the target protein, is linked to the N-terminus of norovirus-derived VP1 protein;

(B) introducing the expression vector into a host cell; and (C) producing a recombinant norovirus VP1 protein from the host cell.

The peptide containing 7-amino acid sequence derived from urate oxidase according to the present invention can improve expression efficiency of a target protein, and furthermore, the fusion protein obtained by binding the peptide to RID, which is well known as a solubility-enhancing protein, improves solubility as well as expression efficiency of the target protein, so that these can be usefully used for production of a recombinant target protein.

Advantageous Effects of Invention

The peptide for enhancing expression efficiency of a target protein according to the present invention can improve expression efficiency of the target protein, and can also be applied with RID known as a solubility-enhancing fusion partner thereof, so that expression level and solubility of the target protein are simultaneously improved. Thus, such a peptide can be usefully used for production of a recombinant target protein.

BRIEF DESCRIPTION OF DRAWINGS

FIG. 1 illustrates experimental results showing an effect of the peptide (eet1) of the present invention on expression efficiency of EGFP protein (A: SDS-PAGE results showing expression of each fusion protein, B: a graph showing each fusion protein's relative expression level in a case where an expression level of a control (EGFP) treated with 80 µM IPTG is taken as 1, and C: a graph showing each fusion protein's relative activity in a case where protein activity of the control treated with 80 µM IPTG is taken as 1).

FIG. 2 illustrates results obtained by comparing effects of the peptide of the present invention or a part thereof on expression efficiency and activity of EGFP protein (A: SDS-PAGE results showing expression of each fusion protein, B: each fusion protein's relative expression level in a case where an expression level of a control (MSEQHAQ (SEQ ID NO: 5)-EGFP) treated with 80 µM IPTG is taken as 1, C: each fusion protein's relative activity in a case where protein activity of the control treated with 80 µM IPTG is taken as 1, and D: a graph showing protein activity per unit protein).

FIG. 3 illustrates a graph showing an effect of the peptide of the present invention on expression of TruB, an *E. coli*-derived protein (A: SDS-PAGE results showing expression of each fusion protein, B: a graph showing each fusion protein's relative expression level in a case where an expression level of a control is taken as 1).

FIG. 4 illustrates SDS-PAGE results (A) showing an effect of the peptide of the present invention on hRID, a solubility-enhancing fusion partner, and a graph (B) showing changes in relative expression level.

FIG. 7A illustrates results obtained by identifying, with SDS-PAGE, solubility of VP1 protein expressed according to an embodiment of the present invention, in which the left panel shows an expression result of VP1 (70 kDa) recombined with MSAVKAA (SEQ ID NO: 1)-RID and the right panel shows a result of a comparative example (VP1 recombined with MSEQ (SEQ ID NO: 15)-RID; 69 kDa).

FIG. 7B illustrates results obtained by identifying, with SDS-PAGE, expression in soluble form of the VP1 protein expressed according to an embodiment of the present invention, in which the left panel shows an expression result of VP1 (70 kDa) recombined with MSAVKAA (SEQ ID NO: 1)-RID, the middle panel shows an expression result of VP1 (70 kDa) recombined with MSAV (SEQ ID NO: 2)-RID, and the right panel shows an expression result of a control (MS-RID).

Figure 8:
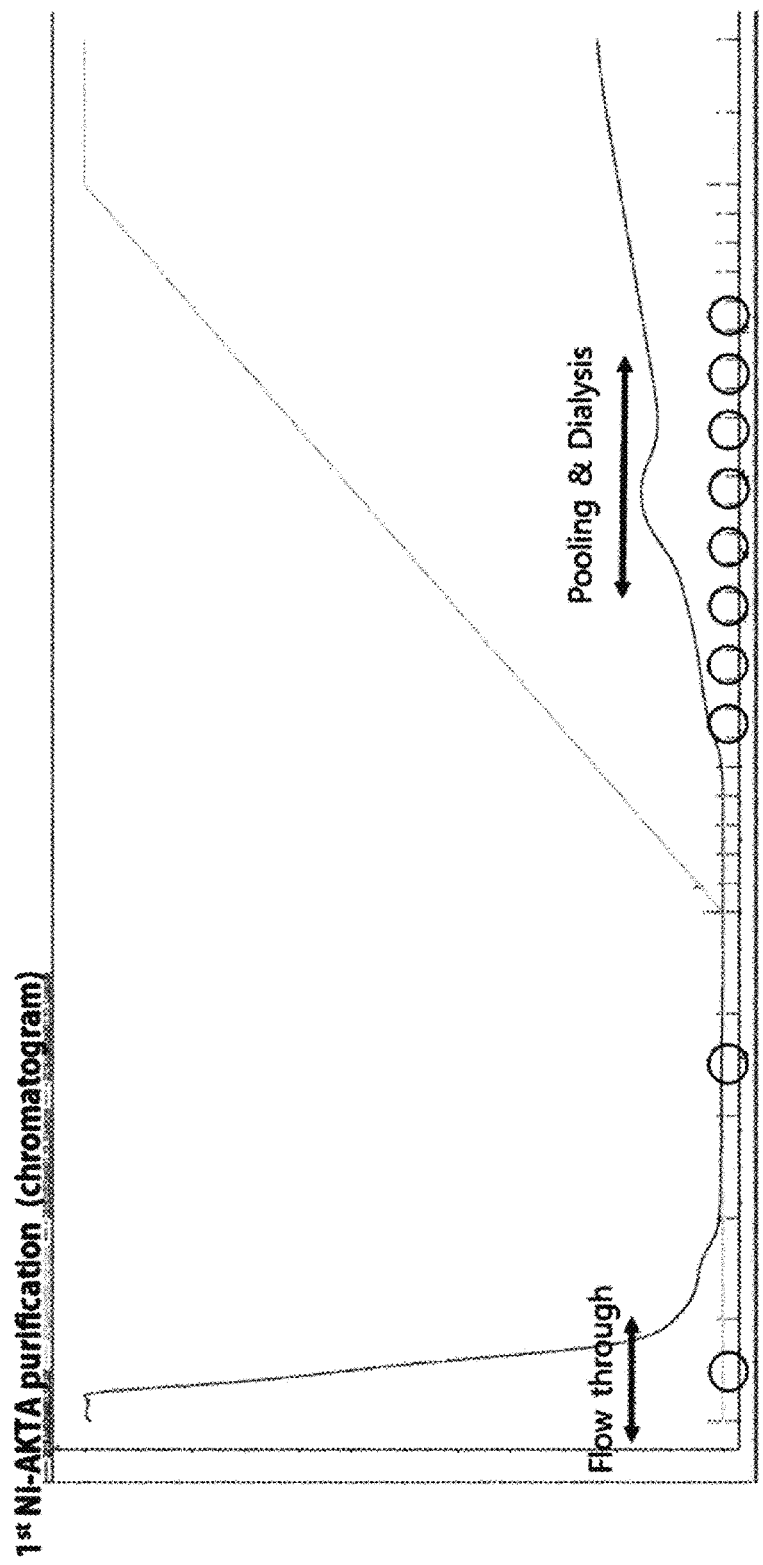

FIG. 8 illustrates a chromatogram result obtained by purifying and identifying, through nickel affinity chromatography, VP1 protein expressed according to an embodiment of the present invention.

Figure 9:
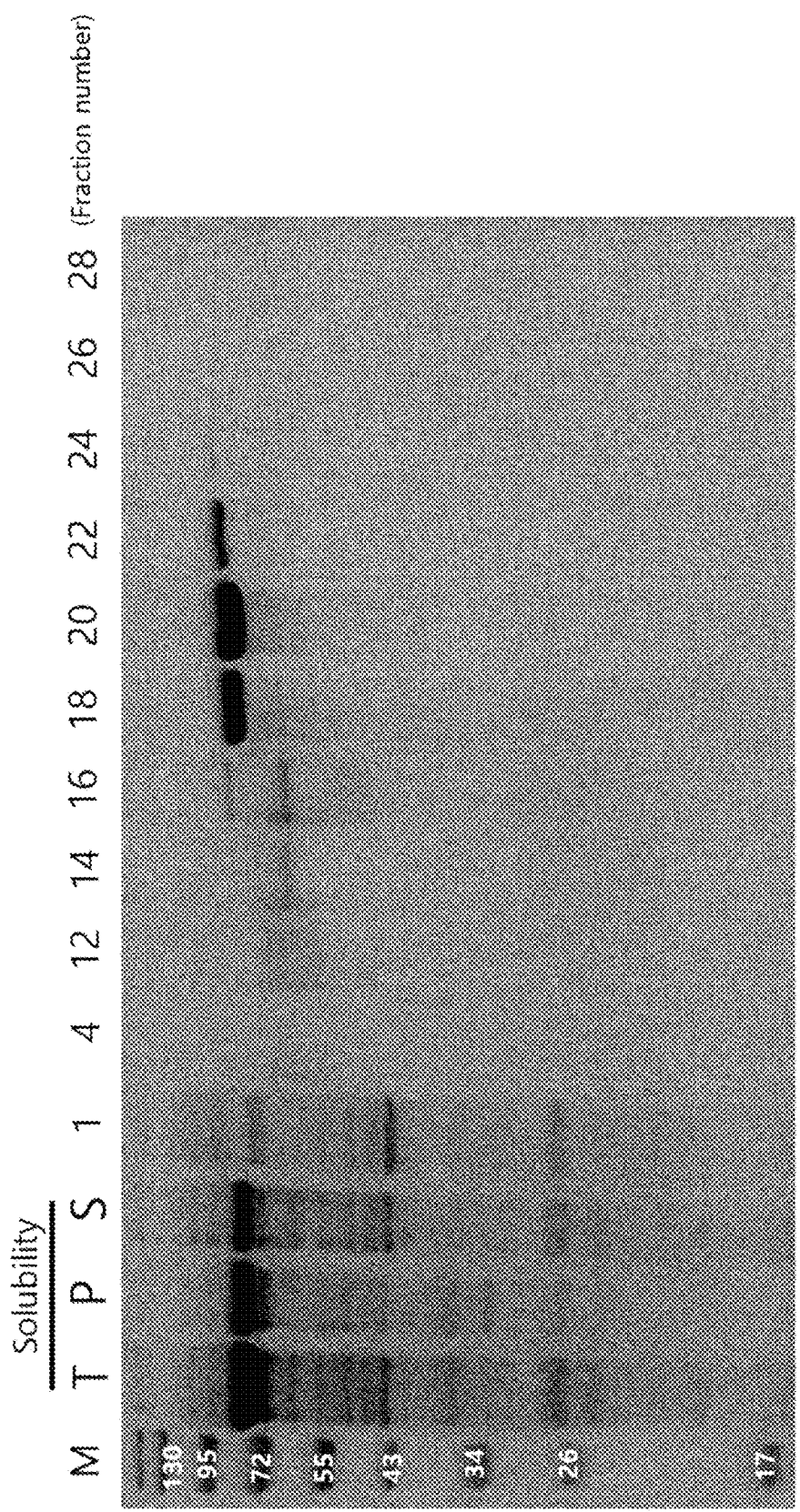

FIG. 9 illustrates results obtained by purifying VP1 protein expressed according to an embodiment of the present invention, and then identifying the same with SDS-PAGE, in which the fractions of lanes 18 to 20 are pooled.

FIG. 10 illustrates results obtained by cleaving norovirus VP1 using TEV protease, and then identifying the same with SDS-PAGE.

Figure 11A:
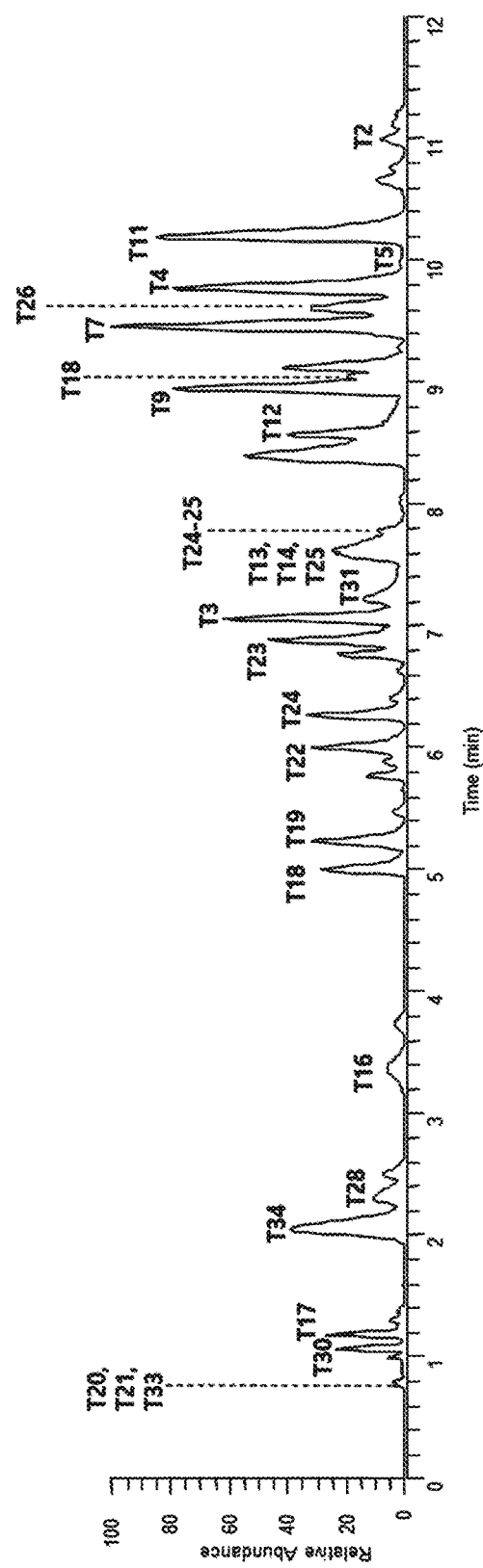
Figure 11B:
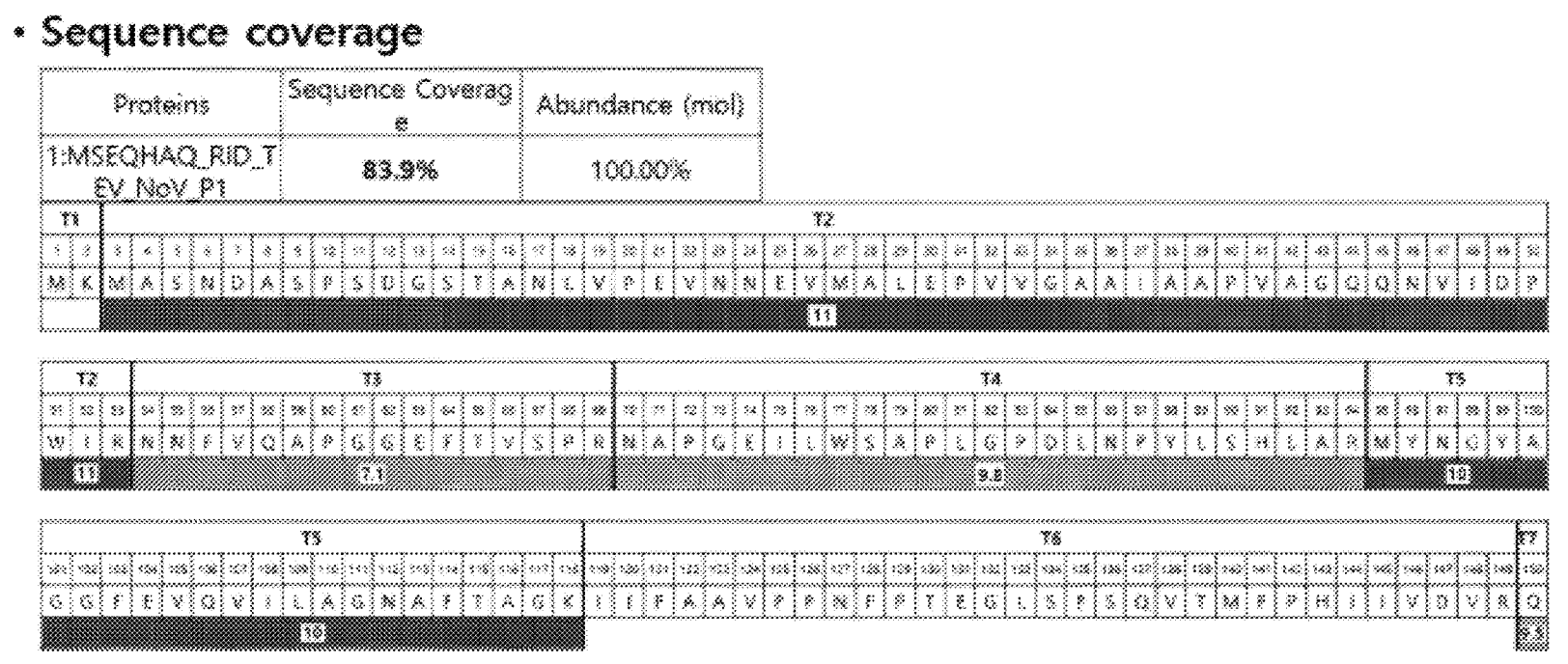
Figure 11C:
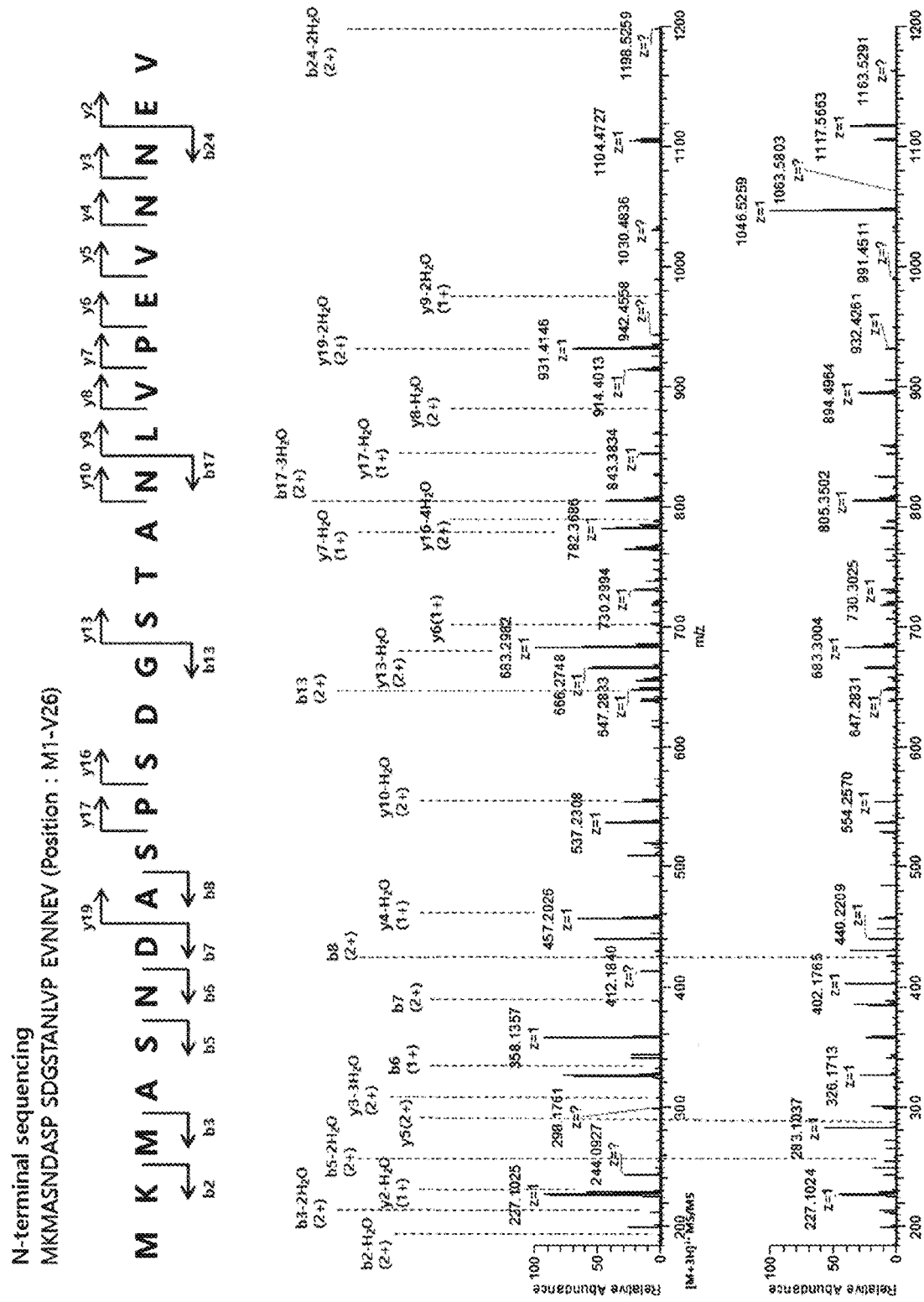
Figure 11D:
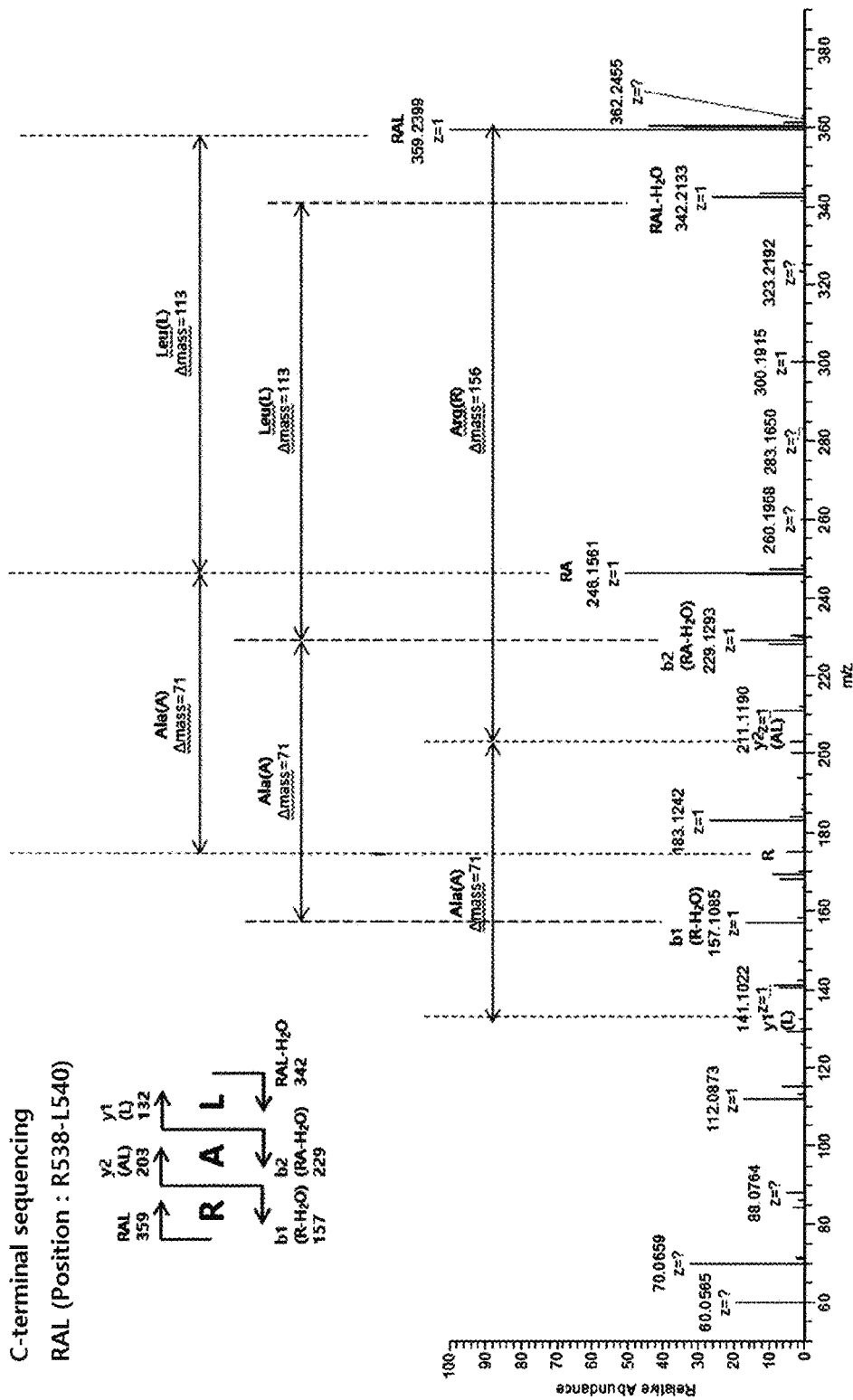

FIG. 11 illustrates results obtained by performing peptide mapping, and N-terminal and C-terminal amino acid sequence analysis, so as to identify whether the protein obtained through expression and purification consists of the VP1 sequence. FIG. 11A illustrates UPLC peaks obtained by performing analysis after trypsin treatment. FIGS. 11B, 11B-A, 11B-B, and 11B-C illustrate results, identifying that as a result of LC-MS/MS analysis of the peptide fragment (SEQ ID NO: 17) appearing in trypsin treatment, such a peptide fragment exhibits an 83.9% match, in terms of amino acid sequence, with the originally expected sequence. FIG. 11C illustrates results, identifying that the protein's N-terminal sequence (SEQ ID NO: 18) matches norovirus VP1. FIG. 11D illustrates results, identifying that the protein's C-terminal sequence matches norovirus VP1.

Figure 12A:
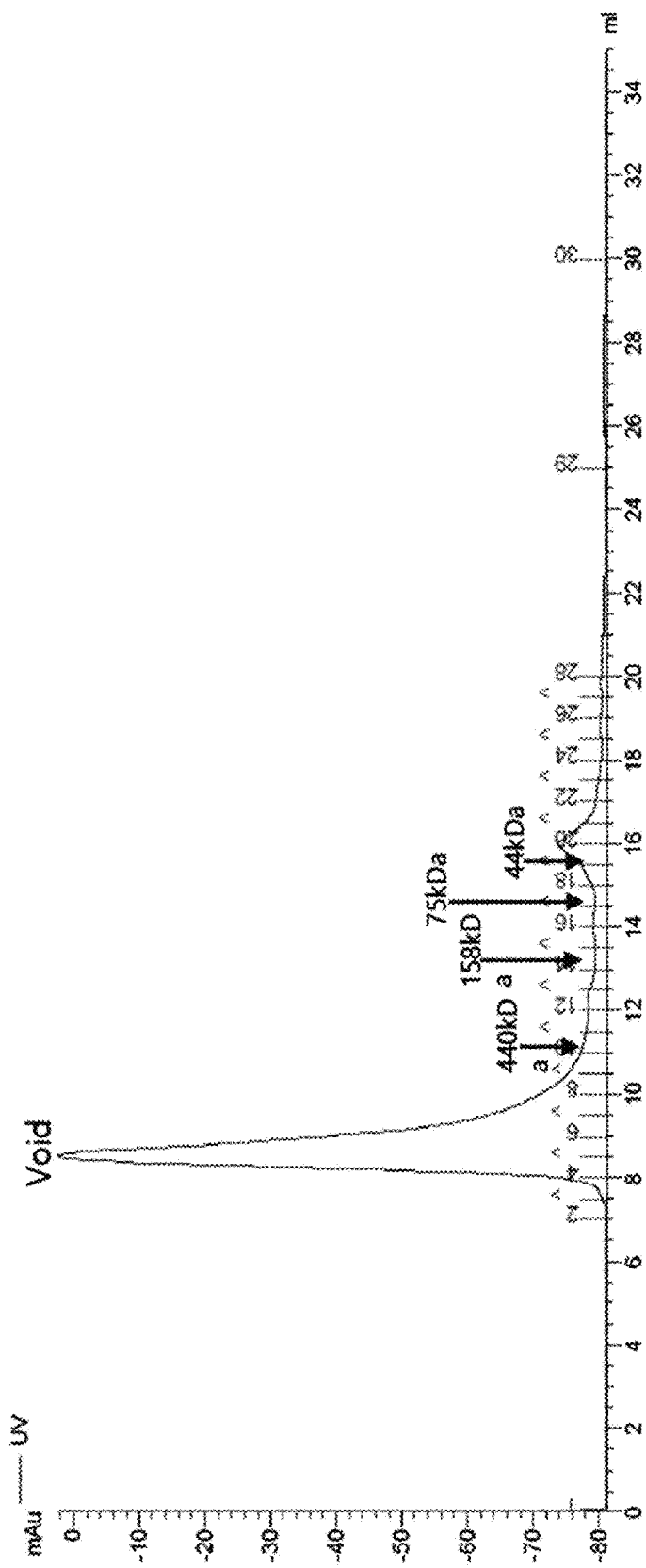

FIG. 12A illustrates a chromatogram showing results obtained by performing size exclusion chromatography in order to purify VLP formed after cleavage with TEV protease.

Figure 12B:
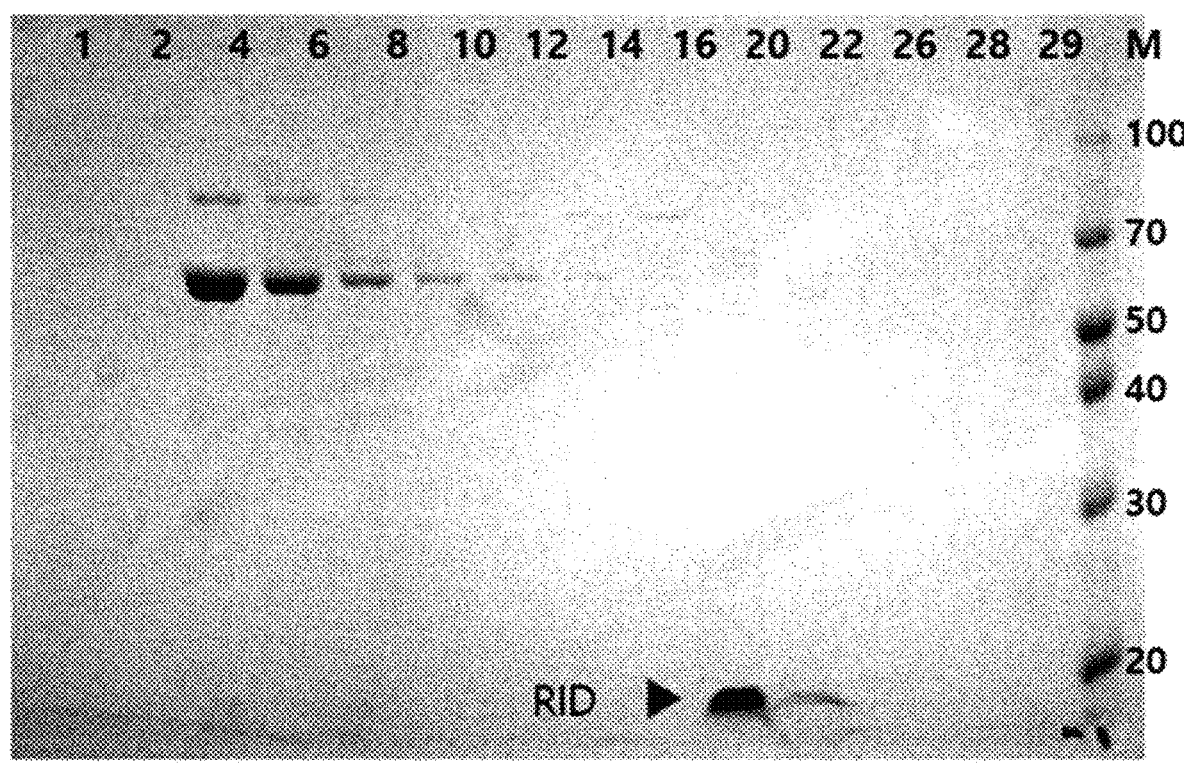

FIG. 12B illustrates results obtained by purifying VLP protein formed after cleavage with TEV protease, and then identifying the same with SDS-PAGE.

Figure 13:
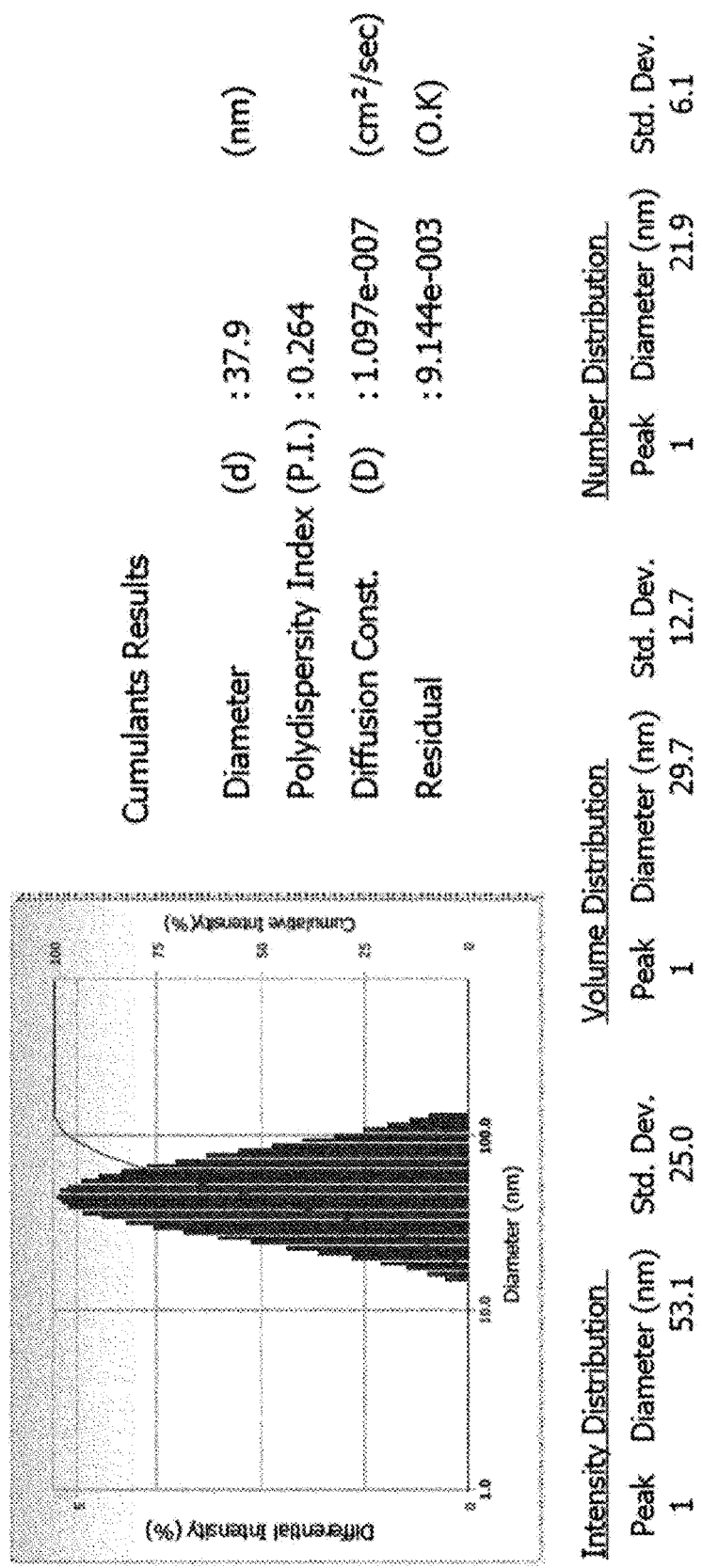

FIG. 13 illustrates results obtained by analyzing the purified VLP through dynamic light scattering (DLS) in order to identify its overall diameter.

Figure 14:
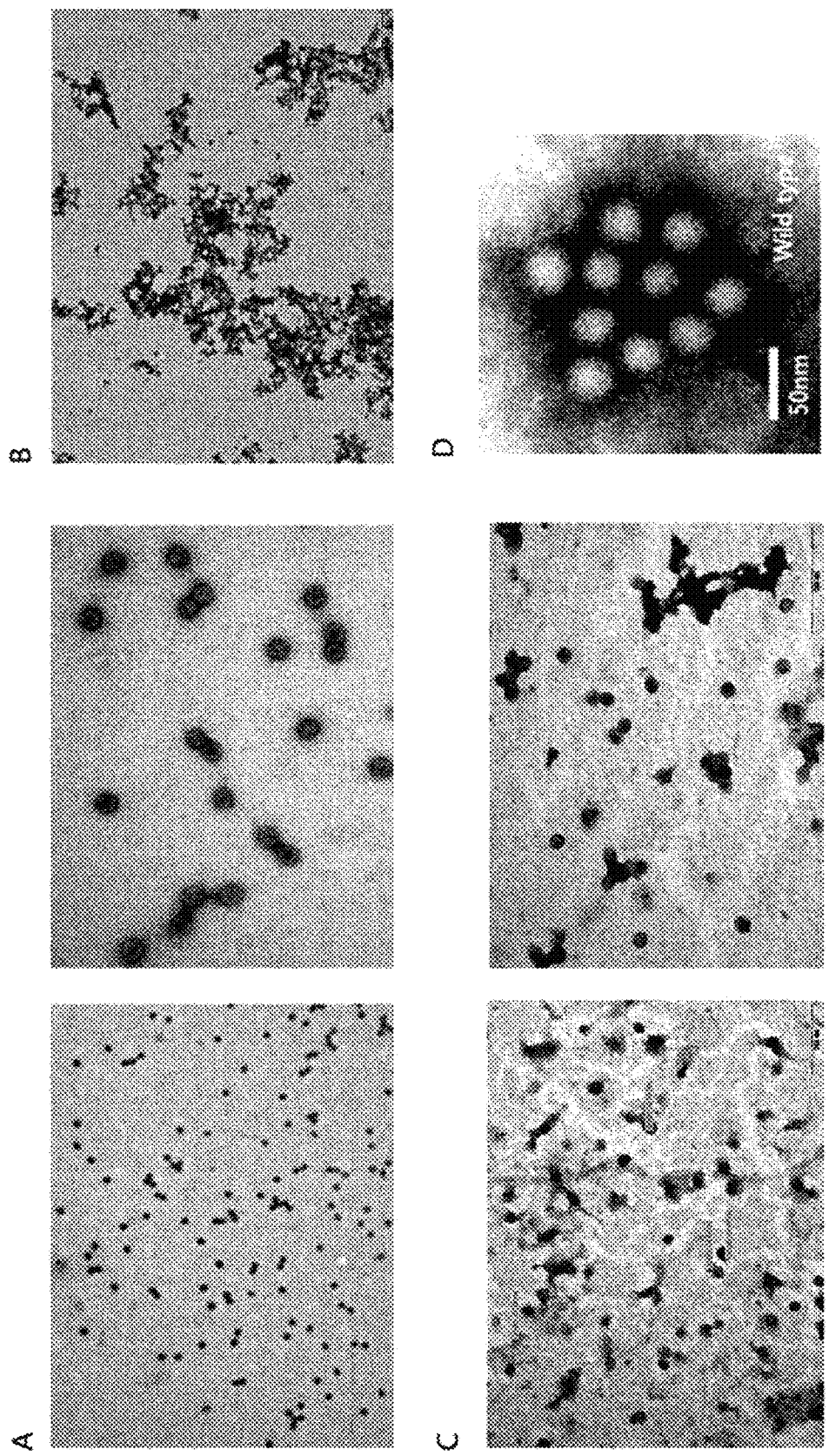

FIG. 14 illustrates results obtained by identifying, using TEM electron microscopy, whether the purified VP1 proteins have formed VLP [A: *E. coli*-derived virus-like particle (VLP) identified through electron microscopy, B: recombinant VP1 protein from which a RID tag containing histidine and TEV recognition sequence has not been removed (failure to form VLP structure), C: norovirus VLPs produced using baculovirus-insect cell system, and D: wild-type norovirus virion].

DETAILED DESCRIPTION OF INVENTION

Hereinafter, various examples are presented to help understand the present invention. The following examples are provided only for easier understanding of the present invention, and the scope of protection of the present invention is not limited to the following examples.

<Experimental Methods>

1. Construction of Protein Expression Vector pGE-LysRS expression vector was used as a protein expression vector (Choi, S. I. et al., Protein solubility and folding enhancement by interaction with RNA, *PLoS ONE* (2008), 3:e2677). In pGE-LysRS whose expression is under control of T7 promoter, the LysRS gene is cleaved using Ndel and one of the cleavage sites present in MCS (Kpn1-BamH1-EcoRV-Sal1-Hind3), and EGFP or hRID, or other proteins were inserted into the same location. Here, the amino acid sequence (eet1) of SEQ ID NO: 1 or a part thereof (eet2, SEQ ID NO: 2) was inserted at the N-terminal position of the inserted protein. Then, target proteins to be expressed were inserted using two restriction enzyme sites in the prepared hRID or MCS of hRID vector containing the amino acid sequence of SEQ ID NO: 1.

2. Protein Expression and SDS-PAGE

The prepared protein expression vector was transformed into BL21 (DE3), BL21 (DE3)-pLysS, or BL21 (DE3)-pLysE competent cells, and culture was performed. All transformed *E. coli* cells were cultured in LB medium containing 50 µg/ml of ampicillin. The *E. coli* cells transformed with BL21*(DE3)-pLysS or BL21*(DE3)-pLysE were cultured in the medium supplemented with 34 µg/ml of chloramphenicol. Different culture temperature was used for each protein, and culture was performed at a condition of 33° C. to 37° C. When the $OD_{600}$ value of *E. coli* reached 0.5 or higher, IPTG was added at a level of 0 µM to 1 mM to activate T7 promoter, and culture was performed at 33° C. or 37° C. for about 3 hours after addition of IPTG so that a sufficient amount of protein can be produced. Sufficiently cultured *E. coli* cells were centrifuged and the supernatant was removed. Then, the resulting *E. coli* harvest was stored.

Next, 0.3 ml of PBS was added to the *E. coli* harvest corresponding to 5 ml of the LB medium, and ultrasonic pulverization was performed to make a lysate. Alternatively, the *E. coli* harvest corresponding to 1 ml was subjected to treatment with 60 μl of B-PER (Thermo Fisher Scientific), together with DNase and lysozyme at appropriate concentrations, thereby obtaining a lysate. Then, the lysate was analyzed with SDS-PAGE.

3. Fluorescence Measurement of EGFP Protein

Fluorescence was measured at Ex 485 nm/Em 520 nm using Fluostar Optima (BMG Labtech) to identify activity of the protein expressed in the sample to be analyzed.

EXAMPLES

Example 1

Effect of Peptide of Present Invention on Expression Efficiency and Activity of EGFP Protein 1-1. SDS-PAGE Analysis In pGE LysRS plasmid, LysRS was removed using NdeI and Hind3 restriction enzymes, and each of two sequences, EGFP gene sequence and a fusion form (eet1-EGFP) obtained by adding, to the N-terminus of the EGFP gene sequence, gene sequence (SEQ ID NO: 3) encoding the amino acid sequence (eet1) of SEQ ID NO: 1, was inserted into the same location. The vector is in the form of being expressed by T7 promoter and being regulated by lac operator, in which promoter activation is regulated by IPTG. The two recombinant plasmids were respectively transformed into BL21*(DE3)-pLysE competent cells, and protein expression was induced at a condition of 37° C. for 3 hours. Here, treatment with IPTG was performed at four concentrations of 0, 20, 40, and 80 μM.

As a result, as illustrated in FIGS. 1A and 1B, it was found that in a case of the fusion form (eet1-EGFP) of the EGFP gene, its expression is induced better than the control (EGFP).

1-2. Protein Activity Assay

In order to check whether the expressed EGFP protein is also functional, for the EGFP sample in lysate form, which had been expressed under each condition, its fluorescence value was measured at 485 nm/520 nm using Fluostar Optima.

As a result, as illustrated in FIG. 1C, it was found that in a case of the fusion form to which eet1 has been added, activity as well as expression of the EGFP protein is increased.

Example 2

Effect of Partial Sequence of Peptide of Present Invention

In order to identify an effect exhibited in a case where a partial sequence (eet2, SEQ ID NO: 2) of the peptide (eet1) identified in Example 1 is fused to a target protein, an EGFP fusion protein was expressed in the same manner as in Example 1. As a control, gene (SEQ ID NO: 6) encoding the lysyl tRNA synthetase-derived amino acid sequence (MSEQHAQ) represented by SEQ ID NO: 5 was used. Here, treatment with IPTG was performed at concentrations of 10, 20, 40, and 80 μM.

Figure 2:
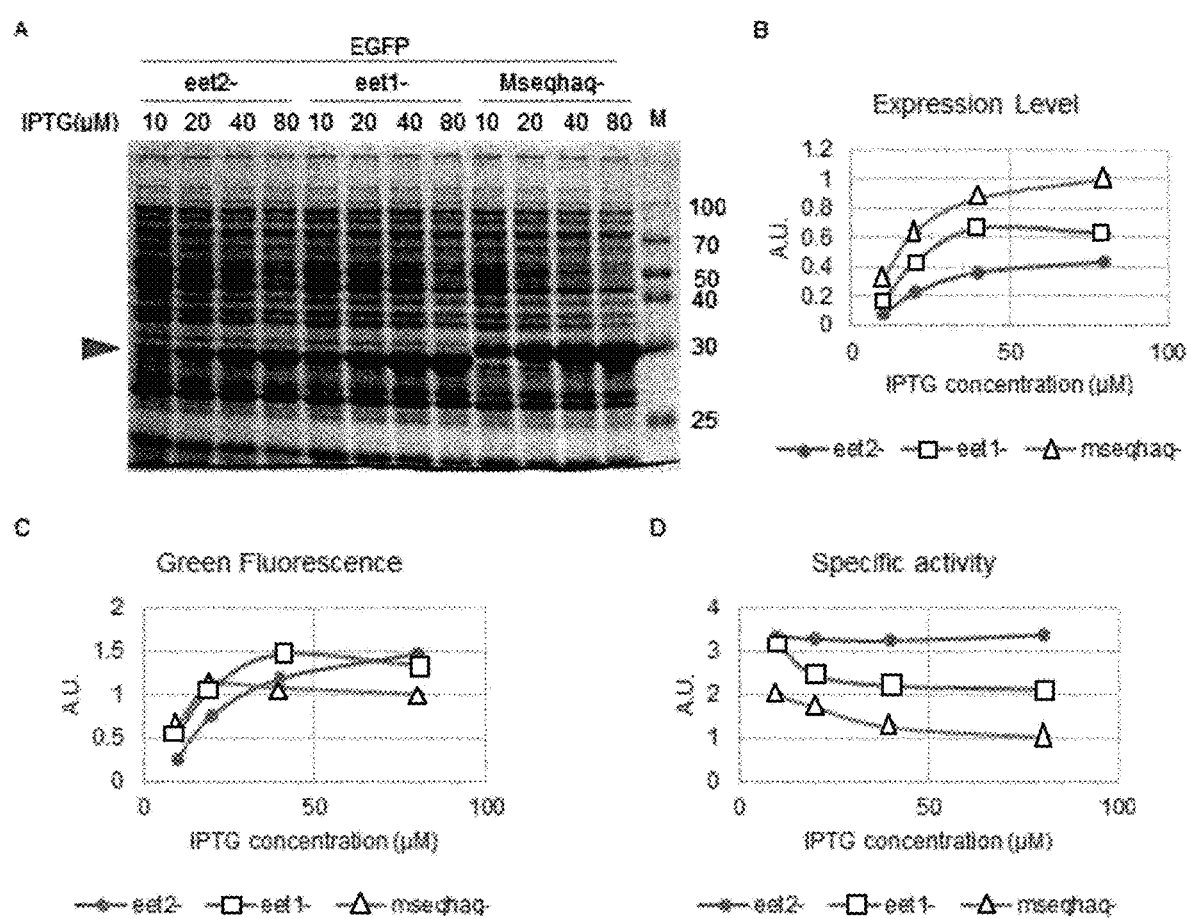

As a result, as illustrated in FIGS. 2A and 2B, the EGFP proteins (eet1-EGFP, eet2-EGFP) obtained by addition of the novel peptide of the present invention exhibit a lower expression level than the control protein (MSEQHAQ (SEQ ID NO: 5)-EGFP) obtained by being fused with the control peptide. However, as illustrated in FIG. 2C, it was found that at the IPTG concentration of 40 μM or higher, a higher amount of active protein is produced in a case of being fused with eet1 or eet2. From these results, it can be seen that in a case of being fused with the eet2 sequence, lower expression level but better protein activity is exhibited than eet1, and the highest amount of active protein is produced at the IPTG concentration of 80 μM (FIGS. 2A to 2C).

In addition, when this was calculated in terms of activity per unit protein, it was identified that in a case of being fused with the eet1 sequence, a high-quality protein can be expressed in an amount equal to or greater than two times the control and that in a case of being fused with the eet2 sequence, a high-quality protein can be expressed in an amount equal to or greater than three times the control (FIG. 2D). From these results, it can be seen that increasing an expression level of highly active protein is substantially better for improving protein expression efficiency than simply increasing an expression level of protein.

Example 3

Effect of Peptide According to Present Invention on Expression Efficiency of TruB and TruB-EGFP Protein In order to examine an effect of the peptide according to the present invention on expression of TruB protein, which is known to be poorly expressed in *E. coli*, the gene sequence encoding TruB protein and the gene sequence encoding TruB-EGFP protein, and their fusion forms, to each of which the nucleotide sequence of SEQ ID NO: 2 had been added, were respectively inserted into pGE LysRS plasmid using the same method as in Example 1. A total of four recombinant plasmids were transformed into BL21*(DE3)-pLysS competent cells, and protein expression was induced at a condition of 37° C. Here, treatment with IPTG was performed at 1 mM concentration, and over-expression was performed for 3 hours.

As a result, the controls (TruB and TruB-EGFP) were barely expressed to the extent that they are obscured by miscellaneous bands; however, in a case where eet1 of SEQ ID NO: 1 is fused to each of the TruB and TruB-EGFP proteins, it was identified that the respective proteins are expressed. Here, it was found that the expression level of the respective proteins is equal to or greater than three times the controls (FIGS. 3A and 3B).

Example 4

Effect of Peptide According to Present Invention on Expression Efficiency of RID Protein In order to examine an effect of the peptide according to the present invention on expression of hRID protein (SEQ ID NO: 7), which had been developed as solubility-enhancing fusion partner, in *E. coli*, its expression level was identified using the same method as in Example 1. Specifically, the gene (SEQ ID NO: 8) encoding hRID protein, and the fusion form (SEQ ID NO: 10), in which an eet1-encoding gene had been linked to the N-terminus of hRID, were respectively inserted into pGE LysRS plasmid. The two recombinant plasmids were transformed into BL21*(DE3)-pLysS competent cells, and protein expression was induced at a condition of 37° C. Here, treatment with IPTG was performed at concentrations of 0, 20, 100, and 1000 μM, and over-expression was performed for 3 hours.

As a result, as illustrated in FIG. 4, it was found that although the control (hRID) is barely expressed, the fusion form (eet1-hRID) obtained by addition of eet1 is well expressed (FIG. 4A). In a case of quantitative analysis of expression level, since the expression level of the control was too low to be used as a baseline, expression level comparison was performed using, as a baseline, the experimental group in which IPTG at 1,000 µM is used (FIG. 4B).

Example 5

Effect of Fusion Protein Containing Peptide and RID According to Present Invention on Expression Efficiency of Three Proteins, CsTA1953, CsTA37, and CsTA422 hRID was used as a fusion partner for increasing expression level and solubility of CsTA1953, CsTA37, and CsTA422 proteins, which are known to be poorly expressed in E. coli or not to be well expressed in a soluble form even in a case of being expressed. In pGE LysRS plasmid, LysRS was cleaved using NdeI and Kpn1, and the gene sequence (SEQ ID NO: 8) encoding hRID or the gene sequence (SEQ ID NO: 10) encoding the eet1-hRID fusion protein was respectively inserted at the same location. Next, CsTA1953 gene, CsTA37 gene, and CsTA422 gene were respectively inserted into the pGE-hRID plasmid and the pGE-eet1-hRID plasmid using BamH1 and Hind3.

A total of six recombinant proteins thus produced were expressed under the same IPTG concentration condition as in Example 4. Among these, for the four recombinant proteins containing CsTA37 and CsTA422, experiments were conducted only at a condition in which treatment with IPTG at 1 mM is performed. These proteins were expressed at a condition of 33° C.

Figure 5:
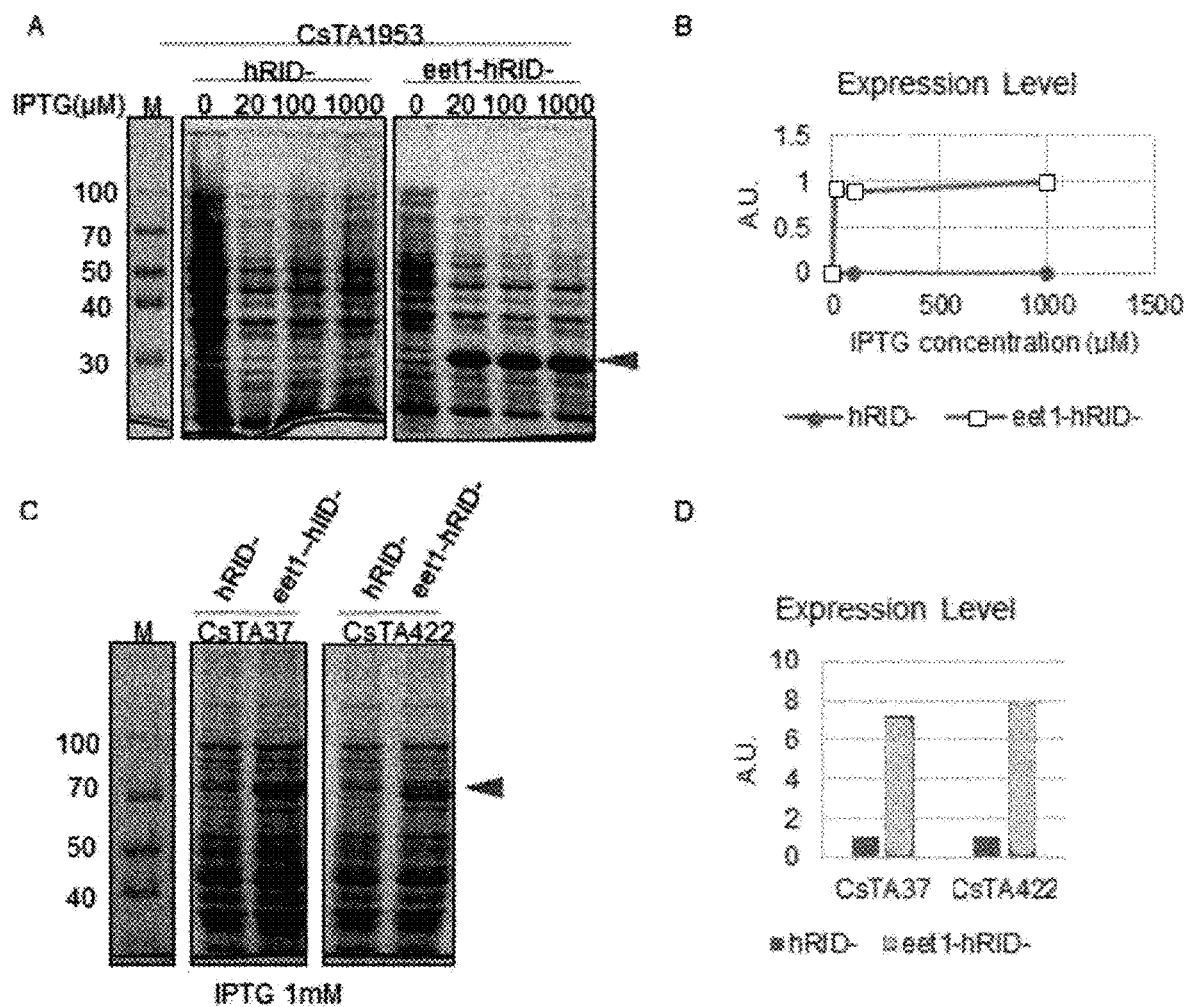
FIG. 5 illustrates graphs showing effects of an hRID fusion, obtained by addition of the peptide of the present invention, on expression efficiency of a target protein.
Figure 6:
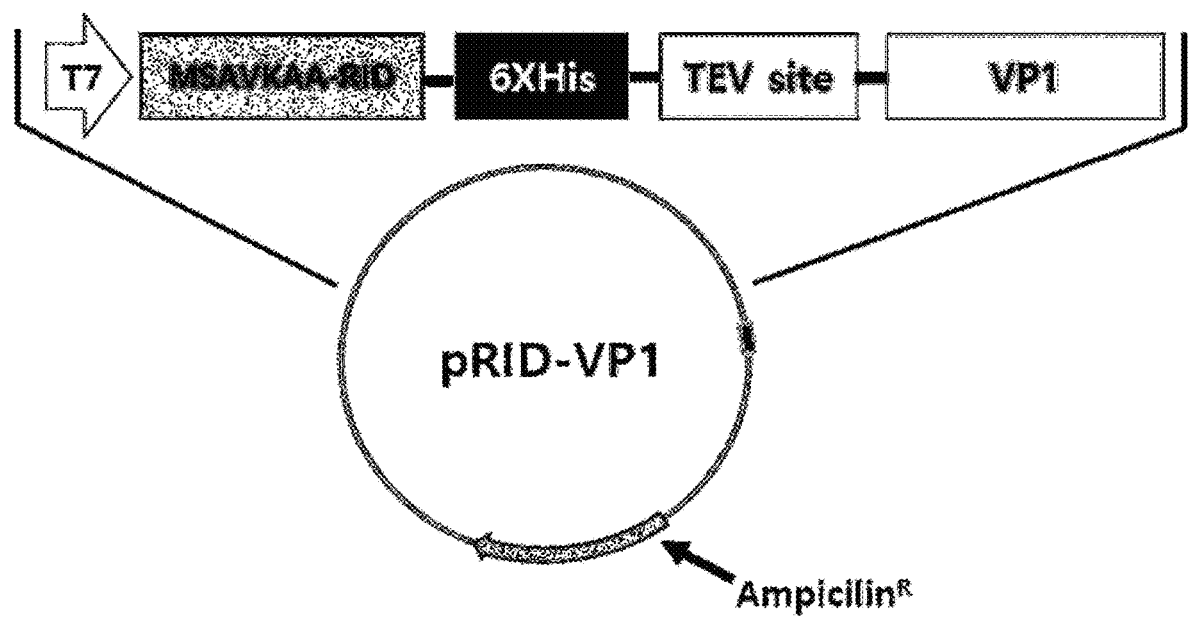
FIG. 6 illustrates a schematic diagram showing a structure of a recombinant expression vector for production of soluble norovirus vaccine according to an embodiment of the present invention.

As a result, as illustrated in FIG. 5, it was found that expression efficiency of the CsTA1953, CsTA37, and CsTA422 proteins is improved in a case where the eet1-hRID fusion protein is bound thereto. Also, in this case, all controls (hRID-) were barely expressed to the extent that they are obscured by miscellaneous bands (FIGS. 5A and 5B). In a case of CsTA1953, since the expression level of the controls was too low, quantitative analysis was performed using, as a baseline, the experimental group in which IPTG at 1,000 µM is used (FIG. 5B). It was found that CsTA37 and CsTA422 exhibit at least 7-fold higher expression than the controls (FIG. 5D).

Example 6

Effect of Fusion Protein Containing Peptide and RID According to Present Invention on Expression Efficiency of Norovirus VP1 Protein 6-1. Construction of Recombinant Expression Vector and Expression of VP1 Protein Norovirus Hu/GII.4/Hiroshima/55/2005/JPN (NCBI access number: AB504310.1)-derived VP1 gene was used for production of norovirus VLP through E. coli, and the VP1 gene in question was obtained through gene synthesis. pGE-LysRS vector was used as an expression vector. This vector is an expression vector made by modifying pGE-MEX-1 (Promega) vector. Specifically, the expression vector was cleaved by treatment with Nde I and BamHI restriction enzymes, and a DNA fragment was inserted into the cleaved expression vector, the DNA fragment consisting of the following sequences in a continuous manner: a polynucleotide sequence (SEQ ID NO: 3) encoding MSAV-KAA (eet1, SEQ ID NO: 1) or a polynucleotide sequence (SEQ ID NO: 4) encoding MSAV (eet 2, SEQ ID NO: 2); a polynucleotide sequence (SEQ ID NO: 11) encoding 6-histidine tag (Histag); a polynucleotide sequence (SEQ ID NO: 12) encoding TEV recognition sequence (ENLYFQ, SEQ ID NO: 16) from which G has been removed; and a polynucleotide sequence (SEQ ID NO: 14) encoding VP1 (SEQ ID NO: 13). The thus completed recombinant plasmid was transformed into the E. coli host HMS174 (DE3). Initial culture for protein expression was performed as follows: Culture was performed at 37° C. for one day in 15 µg/ml of LB medium supplemented with 50 µg/ml of ampicillin, and then 1 ml of E. coli, which had been cultured on the previous day in 15 ml of LB medium supplemented with the same concentration of ampicillin, was added thereto. Culture was performed at 37° C. until the OD$_{600}$ nm reached 0.5 to 0.7. When the appropriate OD value was achieved, overexpression was induced with 1 mM IPTG. After IPTG addition, expression was induced at two different temperatures (37° C., 16° C.). As a comparative example, norovirus VP1 conjugated with RID containing four amino acids, which had been applied in the previous study, was also expressed under the same condition. The expressed protein was collected and checked for solubility through SDS-PAGE.

As a result, as illustrated in FIG. 7A, it was identified that the recombinant VP1 protein is well expressed at 16° C. as well as at 37° C. In addition, as a result of comparison with the comparative example VP1 in terms of expression level, it was found that the recombinant VP1 of the present invention exhibits a markedly increased expression level which is about 2 times or higher than the comparative example VP1 (FIG. 7A). In addition, the (Estimated) norovirus VP1 protein was 59 kDa in size and the VP1 containing RID (8 kDa) was about 70 kDa in size. As a result, it was identified that expression has been induced at an appropriate location.

6-2. Identification of Effect of Partial Sequence of Peptide of Present Invention In order to identify an effect exhibited in a case where norovirus VP1 is fused with a partial sequence (eet2, SEQ ID NO: 2) of the peptide (eet1, SEQ ID NO: 1) identified in Example 6-1, the VP1 protein was expressed in the same manner as in Example 6-1. The proteins, which were expressed at 37° C. for 3 hours after addition of 1 mM IPTG, were collected and checked for solubility through SDS-PAGE.

As a result, as illustrated in FIG. 7B, it was identified that the VP1 protein is not expressed in the control in which MS-RID is fused therewith, and a case where VP1 is fused with eet2 shows a similar expression level to eet1.

6-3. Purification of Norovirus VP1

The proteins, for which solubility had been identified, were purified through nickel (Ni) affinity chromatography. Purification was conducted after E. coli was harvested in an amount of 500 ml, which had been ultimately obtained via 3 ml and 50 ml, using the same culture method as described above. Specifically, equilibrium was first made with A buffer [50 mM Tris-HCl (pH 7.5), 300 mM sodium chloride, 5% glycerol, 0.1 mM 2-mercaptoethanol, and 10 mM imidazole], and equilibrated Ni-NTA column (GE Healthcare Life Sciences, Little Chalfont, Buckinghamshire, UK) was used to purify sample proteins. Following the A buffer, B buffer [50 mM Tris-HCl (pH 7.5), 300 mM sodium chloride, 5% glycerol, 0.1 mM 2-mercaptoethanol, and 300 mM imidazole] was used to elute the proteins with linear gradient imidazole in a range of 10 to 300 mM. Target protein-containing fractions were identified through SDS-PAGE. Then, the fractions in question were collected and dialyzed using C buffer (store buffer) [50 mM Tris-HCl (pH 8.5), 10 mM NaCl, 0.1% 2-mercaptoethanol]. The concentration of finally-purified proteins was quantified using BSA (Amresco, Solon, Ohio, USA). The purified VP1 protein was mixed with 20% glycerol at a 1:1 ratio, and then stored at −20° C.

The results obtained by identifying the purified MSAV-KAA (SEQ ID NO: 1)-RID-VP1 fusion protein with nickel affinity chromatography and the results obtained by identifying purification through SDS-PAGE are illustrated in FIGS. 8 and 9. Purification was successfully conducted. After the first purification, the conjugating protein (tag) containing MSAVKAA (SEQ ID NO: 1)-RID was also successfully removed through TEV protease. Subsequently, TEV, cleaved tag, and uncleaved-fusion protein were separated through 2nd Ni-affinity chromatography to obtain completely purified VP1 (FIG. 10).

6-4 Amino Acid Sequence Analysis of Purified VP1

In order to check whether the protein obtained through the expression and purification experiments consists of the expected VP1 sequence, peptide mapping, and N-terminal and C-terminal sequencing were conducted by making a request to ISS (www.isslab.co.kr), a specialized analysis organization. First, it was identified that as a result of LC-MS/MS analysis of the peptide fragment appearing in trypsin treatment, such a peptide fragment exhibits an 83.9% match, in terms of amino acid sequence, with the originally expected sequence. It was identified that as a result of comparison of the N-terminal sequence 26-mer and the C-terminal sequence 3-mer, a match with NoV VP1 is observed (FIG. 11).

6-5. Size Exclusion Chromatography

Biochemical analysis was performed to check whether the dimers of VP1 protein, obtained by cleavage with protease after TEV cleavage, form VLP. Specifically, size exclusion chromatography was performed at 4° C. through a Superdex-200 analytical gel-filtration column.

On the previous day, the fusion protein was cleaved at 16° C. for one day using AcTEV protease. The column was subjected to equilibrium with a buffer [ammonium acetate 250 mM (pH 6.0)]. After completion of the equilibrium, the VP1 sample from which the fusion partner protein had been cleaved was loaded thereon and purification was performed. After purification, calibration was performed using ferritin (440 kDa), aldolase (158 kDa), conalbumin (75 kDa), ovalbumin (44 kDa), and Blue Dextran 2000 (GE Healthcare), thereby determining the molecular weight of a protein which had appeared as a peak on the chromatogram.

From the viewpoints that the norovirus VLP showed a molecular weight of 10 MDa according to the results of the previous study and that the maximum purification limit of the column used by the present inventors was 800 kDa, it was assumed that VLP would be purified in void in a case of being properly formed. As a result of checking the chromatogram, it was found that in the void, there is a high peak appearing as norovirus VLP (FIG. 12A), and it was found that as a result of checking the purified and harvested fractions with SDS-PAGE, the peak appearing in the void corresponds to norovirus VLP (FIG. 12B). In addition, it was found that hRBD resulting from cleavage with TEV protease has also been purified by chromatography.

6-6. Dynamic Light Scattering Analysis

In order to identify the overall diameter of purified virus-like particles (VLPs), analysis was performed through dynamic light scattering (DLS).

As a result, it was identified that their overall diameter is observed in a size similar to 30 to 40 nm which the wild-type norovirus shows (FIG. 13).

6-7. Identification of VLP Formation Through Electron Microscopy

In order to check whether the VP1 proteins purified in the void have formed VLP, observations were made with electron microscopy. Purified norovirus VLPs were first placed on a copper grid for 1 minute and then stained for 15 seconds using 2% uranyl acetate. The pretreated sample was dried at room temperature for 30 minutes and then photographed using transmission electron microscopy (TEM; JEM-1011, JEOL, Japan). The above experiment was carried out at the Research Support Department of Yonsei Biomedical Research Center, Yonsei University College of Medicine.

As a result, as illustrated in FIG. 14, it was found that the purified VP1 proteins form VLP. The thus identified VLP's diameter was 34 nm, which was similar to that of the norovirus VLP produced using the baculovirus-insect cell expression system and the wild-type norovirus. On the other hand, it was found that VP1s, each of which has not been cleaved with TEV protease and with each of which hRBD is fused, do not form VLP and are aggregated (FIG. 14).

As described above, the present invention has been described by way of preferred embodiments. It will be understood by those skilled in the art that various changes and modifications can be made without departing from essential features of the present invention. Therefore, it is to be understood that the above-described examples are illustrative in all aspects and not restrictive. It should be interpreted that the scope of the present invention is shown not in the above-stated description but in the claims, and that all differences falling under the scope equivalent thereto are encompassed by the present invention.

The invention claimed is:

1. A fusion protein comprising:
   (a) a peptide for enhancing expression efficiency of a target protein, and
   (b) a target protein,
   wherein the peptide is linked to the N-terminus of the target protein and wherein the peptide consists of the amino acid sequence represented by SEQ ID NO: 1.

2. The fusion protein according to claim 1, wherein the amino acid sequence of SEQ ID NO: 1 is derived from urate oxidase.

3. The fusion protein according to claim 1, wherein the peptide contains the amino acid sequence represented by SEQ ID NO: 2.

4. The fusion protein according to claim 1, wherein the target protein is at least one selected from the group consisting of an antigen, an antibody, a cell receptor, an enzyme, a structural protein, a serum protein, and a cellular protein.

5. The fusion protein according to claim 1, further comprising:
   an RNA interacting domain (RID) as a fusion partner of the fusion protein, wherein the RID contains the amino acid sequence represented by SEQ ID NO: 7.

6. The fusion protein according to claim 5, wherein the fusion protein contains the amino acid sequence represented by SEQ ID NO: 9.

7. The fusion protein according to claim 5, wherein the target protein is norovirus-derived VP1 protein.

8. A method for producing a soluble target protein comprising the fusion protein according to claim 5, the method comprising the steps of:
   (A) constructing an expression vector that comprises:
      (a) a polynucleotide encoding the target protein,
      (b) a polynucleotide linked to the 5'-end of the polynucleotide encoding the target protein and that encodes the peptide that enhances expression efficiency of the target protein, and
      (c) a polynucleotide encoding the RID that increases solubility of the target protein;
   (B) introducing the expression vector into a host cell to prepare a transformant; and
   (C) culturing the transformant so that expression of a recombinant target protein is induced, and obtaining the recombinant target protein.

* * * * *

SEQUENCE LISTING

<160> NUMBER OF SEQ ID NOS: 18

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Met Ser Ala Val Lys Ala Ala
1               5

<210> SEQ ID NO 2
<211> LENGTH: 4

```
<212> TYPE: PRT
<213> ORGANISM: Artificial Sequence
<220> FEATURE:
<223> OTHER INFORMATION: synthetic peptide

<400> SEQUENCE: 2

Met Ser Ala Val
1

<210> SEQ ID NO 3
<211> LENGTH: 21
<212> TYPE: DNA
<213> ORGANISM: Artificial Sequence
<220> FEATURE:
<223> OTHER INFORMATION: synthetic olignucleotide

<400> SEQUENCE: 3
atgtccgcag taaaagcagc c                                              21

<210> SEQ ID NO 4
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 4
atgtccgcag ta                                                        12

<210> SEQ ID NO 5
<211> LENGTH: 7
<212> TYPE: PRT
<213> ORGANISM: Artificial Sequence
<220> FEATURE:
<223> OTHER INFORMATION: synthetic peptide

<400> SEQUENCE: 5

Met Ser Glu Gln His Ala Gln
1               5

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 6
atgtctgaac aacacgcaca g                                              21

<210> SEQ ID NO 7
<211> LENGTH: 71
<212> TYPE: PRT
<213> ORGANISM: Artificial Sequence
<220> FEATURE:
<223> OTHER INFORMATION: Synthetic peptide

<400> SEQUENCE: 7

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Glu Lys Gln Leu
        35                  40                  45

Ser Gln Ala Thr Ala Ala Ala Thr Asn His Thr Thr Asp Asn Gly Val
```

Gly Pro Glu Glu Glu Ser Val
65                  70

<210> SEQ ID NO 8
<211> LENGTH: 213
<212> TYPE: DNA
<213> ORGANISM: Artificial Sequence
<220> FEATURE:
<223> OTHER INFORMATION: synthetic oligonucleotide

<400> SEQUENCE: 8
atggcggccg tgcaggcggc cgaggtgaaa gtggatggca gcgagccgaa actgagcaag    60
aatgagctga agagacgcct gaaagctgag aagaaagtag cagagaagga ggccaaacag   120
aaagagctca gtgagaaaca gctaagccaa gccactgctg ctgccaccaa ccacaccact   180
gataatggtg tgggtcctga ggaagagagc gtg                                213

<210> SEQ ID NO 9
<211> LENGTH: 77
<212> TYPE: PRT
<213> ORGANISM: Artificial Sequence
<220> FEATURE:
<223> OTHER INFORMATION: synthetic peptide

<400> SEQUENCE: 9

Met Ser Ala Val Lys Ala Ala Ala Ala Val Gln Ala Ala Glu Val Lys
1               5                   10                  15

Val Asp Gly Ser Glu Pro Lys Leu Ser Lys Asn Glu Leu Lys Arg Arg
            20                  25                  30

Leu Lys Ala Glu Lys Lys Val Ala Glu Lys Glu Ala Lys Gln Lys Glu
        35                  40                  45

Leu Ser Glu Lys Gln Leu Ser Gln Ala Thr Ala Ala Thr Asn His
    50                  55                  60

Thr Thr Asp Asn Gly Val Gly Pro Glu Glu Glu Ser Val
65                  70                  75

<210> SEQ ID NO 10
<211> LENGTH: 231
<212> TYPE: DNA
<213> ORGANISM: Artificial Sequence
<220> FEATURE:
<223> OTHER INFORMATION: synthetic oligonucleotide

<400> SEQUENCE: 10
atgtccgcag taaaagcagc cgcggccgtg caggcggccg aggtgaaagt ggatggcagc    60
gagccgaaac tgagcaagaa tgagctgaag agacgcctga agctgagaa gaaagtagca   120 gagaaggagg ccaaacagaa agagctcagt gagaaacagc taagccaagc cactgctgct   180
gccaccaacc acaccactga taatggtgtg ggtcctgagg aagagagcgt g            231

<210> SEQ ID NO 11
<211> LENGTH: 18
<212> TYPE: DNA
<213> ORGANISM: Artificial Sequence
<220> FEATURE:
<223> OTHER INFORMATION: synthetic oligonudleotide

<400> SEQUENCE: 11
caccatcacc atcaccat                                                  18

<210> SEQ ID NO 12
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 12
gaaaacctgt attttcag                                              18

<210> SEQ ID NO 13
<211> LENGTH: 1620
<212> TYPE: PRT
<213> ORGANISM: Artificial Sequence
<220> FEATURE:
<223> OTHER INFORMATION: synthetic peptide

<400> SEQUENCE: 13

Met Glu Thr Leu Tyr Ser Met Glu Thr Ala Leu Ala Ser Glu Arg Ala
1               5                   10                  15

Ser Asn Ala Ser Pro Ala Leu Ala Ser Glu Arg Pro Arg Ala Ser Glu
            20                  25                  30

Arg Ala Ser Pro Gly Leu Tyr Ser Glu Arg Thr His Arg Ala Leu Ala
        35                  40                  45

Ala Ser Asn Leu Glu Ala Val Ala Leu Pro Arg Ala Gly Leu Ala Val
    50                  55                  60

Ala Leu Ala Ser Asn Ala Ser Asn Gly Leu Ala Val Ala Leu Met Glu
65                  70                  75                  80

Thr Ala Leu Ala Leu Glu Ala Gly Leu Ala Pro Arg Ala Val Ala Leu
                85                  90                  95

Val Ala Leu Gly Leu Tyr Ala Leu Ala Ala Leu Ala Ile Leu Glu Ala
            100                 105                 110

Leu Ala Ala Leu Ala Pro Arg Ala Val Ala Leu Ala Leu Ala Gly Leu
        115                 120                 125

Tyr Gly Leu Asn Gly Leu Asn Ala Ser Asn Val Ala Leu Ile Leu Glu
    130                 135                 140

Ala Ser Pro Pro Arg Ala Thr Arg Pro Ile Leu Glu Ala Arg Gly Ala
145                 150                 155                 160

Ser Asn Ala Ser Asn Pro His Glu Val Ala Leu Gly Leu Asn Ala Leu
                165                 170                 175

Ala Pro Arg Ala Gly Leu Tyr Gly Leu Tyr Gly Leu Ala Pro His Glu
            180                 185                 190

Thr His Arg Val Ala Leu Ser Glu Arg Pro Arg Ala Ala Arg Gly Ala
        195                 200                 205

Ser Asn Ala Leu Ala Pro Arg Ala Gly Leu Tyr Gly Leu Ala Ile Leu
    210                 215                 220

Glu Leu Glu Ala Thr Arg Pro Ser Glu Arg Ala Leu Ala Pro Arg Ala
225                 230                 235                 240

Leu Glu Ala Gly Leu Tyr Pro Arg Ala Ala Ser Pro Leu Glu Ala Ala
                245                 250                 255

Ser Asn Pro Arg Ala Thr Tyr Arg Leu Glu Ala Ser Glu Arg His Ile
            260                 265                 270

Ser Leu Glu Ala Ala Leu Ala Ala Arg Gly Met Glu Thr Thr Tyr Arg
        275                 280                 285

Ala Ser Asn Gly Leu Tyr Thr Tyr Arg Ala Leu Ala Gly Leu Tyr Gly
    290                 295                 300

Leu Tyr Pro His Glu Gly Leu Ala Val Ala Leu Gly Leu Asn Val Ala

-continued

```
                305                 310                 315                 320
        Leu Ile Leu Glu Leu Glu Ala Ala Leu Ala Gly Leu Tyr Ala Ser Asn
                        325                 330                 335

Ala Leu Ala Pro His Glu Thr His Arg Ala Leu Ala Gly Leu Tyr Leu
                        340                 345                 350

Tyr Ser Ile Leu Glu Ile Leu Glu Pro His Glu Ala Leu Ala Ala Leu
                        355                 360                 365

Ala Val Ala Leu Pro Arg Ala Pro Arg Ala Ala Ser Asn Pro His Glu
                        370                 375                 380

Pro Arg Ala Thr His Arg Gly Leu Ala Gly Leu Tyr Leu Glu Ala Ser
        385                 390                 395                 400

Glu Arg Pro Arg Ala Ser Glu Arg Gly Leu Asn Val Ala Leu Thr His
                        405                 410                 415

Arg Met Glu Thr Pro His Glu Pro Arg Ala His Ile Ser Ile Leu Glu
                        420                 425                 430

Ile Leu Glu Val Ala Leu Ala Ser Pro Val Ala Leu Ala Arg Gly Gly
                        435                 440                 445

Leu Asn Leu Glu Ala Gly Leu Ala Pro Arg Ala Val Ala Leu Leu Glu
                        450                 455                 460

Ala Ile Leu Glu Pro Arg Ala Leu Glu Ala Pro Arg Ala Ala Ser Pro
        465                 470                 475                 480

Val Ala Leu Ala Arg Gly Ala Ser Asn Ala Ser Asn Pro His Glu Thr
                        485                 490                 495

Tyr Arg His Ile Ser Thr Tyr Arg Ala Ser Asn Gly Leu Asn Ser Glu
                        500                 505                 510

Arg Ala Ser Asn Ala Ser Pro Ser Glu Arg Thr His Arg Ile Leu Glu
                        515                 520                 525

Leu Tyr Ser Leu Glu Ala Ile Leu Glu Ala Leu Ala Met Glu Thr Leu
                        530                 535                 540

Glu Ala Thr Tyr Arg Thr His Arg Pro Arg Ala Leu Glu Ala Ala Arg
        545                 550                 555                 560

Gly Ala Leu Ala Ala Ser Asn Ala Ser Asn Ala Leu Ala Gly Leu Tyr
                        565                 570                 575

Ala Ser Pro Ala Ser Pro Val Ala Leu Pro His Glu Thr His Arg Val
                        580                 585                 590

Ala Leu Ser Glu Arg Cys Tyr Ser Ala Arg Gly Val Ala Leu Leu Glu
                        595                 600                 605

Ala Thr His Arg Ala Arg Gly Pro Arg Ala Ser Glu Arg Pro Arg Ala
                        610                 615                 620

Ala Ser Pro Pro His Glu Ala Ser Pro His Glu Ile Leu Glu Pro
        625                 630                 635                 640

His Glu Leu Glu Ala Val Ala Leu Pro Arg Ala Pro Arg Ala Thr His
                        645                 650                 655

Arg Val Ala Leu Gly Leu Ala Ser Glu Arg Ala Arg Gly Thr His Arg
                        660                 665                 670

Leu Tyr Ser Pro Arg Ala Pro His Glu Thr His Arg Val Ala Leu Pro
                        675                 680                 685

Arg Ala Val Ala Leu Leu Glu Ala Thr His Arg Val Ala Leu Gly Leu
                        690                 695                 700

Ala Gly Leu Ala Met Glu Thr Thr His Arg Ala Ser Asn Ser Glu Arg
        705                 710                 715                 720

Ala Arg Gly Pro His Glu Pro Arg Ala Ile Leu Glu Pro Arg Ala Leu
                        725                 730                 735
```

Glu Ala Gly Leu Ala Leu Tyr Ser Leu Glu Ala Pro His Glu Thr His
                740                 745                 750

Arg Gly Leu Tyr Pro Arg Ala Ser Glu Arg Ser Glu Arg Ala Leu Ala
                755                 760                 765

Pro His Glu Val Ala Leu Val Ala Leu Gly Leu Asn Pro Arg Ala Gly
            770                 775                 780

Leu Asn Ala Ser Asn Gly Leu Tyr Ala Arg Gly Cys Tyr Ser Thr His
785                 790                 795                 800

Arg Thr His Arg Ala Ser Pro Gly Leu Tyr Val Ala Leu Leu Glu Ala
                805                 810                 815

Leu Glu Ala Gly Leu Tyr Thr His Arg Thr His Arg Gly Leu Asn Leu
                820                 825                 830

Glu Ala Ser Glu Arg Pro Arg Ala Val Ala Leu Ala Ser Asn Ile Leu
                835                 840                 845

Glu Cys Tyr Ser Thr His Arg Pro His Glu Ala Arg Gly Gly Leu Tyr
            850                 855                 860

Ala Ser Pro Val Ala Leu Thr His Arg His Ile Ser Ile Leu Glu Pro
865                 870                 875                 880

Arg Ala Gly Leu Tyr Thr His Arg Ala Arg Gly Thr His Arg Thr Tyr
                885                 890                 895

Arg Ala Arg Gly Met Glu Thr Ala Ser Asn Leu Glu Ala Ala Leu Ala
                900                 905                 910

Ser Glu Arg Gly Leu Asn Ala Ser Asn Thr Arg Pro Ala Ser Asn Ala
                915                 920                 925

Ser Asn Thr Tyr Arg Ala Ser Pro Pro Arg Ala Thr His Arg Gly Leu
                930                 935                 940

Ala Gly Leu Ala Ile Leu Glu Pro Arg Ala Ala Leu Ala Pro Arg Ala
945                 950                 955                 960

Leu Glu Ala Gly Leu Tyr Thr His Arg Pro Arg Ala Ala Ser Pro Pro
                965                 970                 975

His Glu Val Ala Leu Gly Leu Tyr Leu Tyr Ser Ile Leu Glu Gly Leu
            980                 985                 990

Asn Gly Leu Tyr Met Glu Thr Leu Glu Ala Thr His Arg Gly Leu Asn
                995                 1000                1005

Thr His Arg Thr His Arg Leu Tyr Ser Gly Leu Tyr Ala Ser Pro
        1010                1015                1020

Gly Leu Tyr Ser Glu Arg Thr His Arg Ala Arg Gly Gly Leu Tyr
        1025                1030                1035

His Ile Ser Leu Tyr Ser Ala Leu Ala Thr His Arg Val Ala Leu
        1040                1045                1050

Ser Glu Arg Thr His Arg Gly Leu Tyr Ser Glu Arg Val Ala Leu
        1055                1060                1065

Ala Ser Pro Pro His Glu Thr His Arg Pro Arg Ala Leu Tyr Ser
        1070                1075                1080

Leu Glu Ala Gly Leu Tyr Ser Glu Arg Val Ala Leu Gly Leu Asn
        1085                1090                1095

Pro His Glu Ala Leu Ala Thr His Arg Ala Ser Pro Thr His Arg
        1100                1105                1110

Ala Ser Pro Ala Ser Asn Ala Ser Pro Pro His Glu Gly Leu Ala
        1115                1120                1125

Thr His Arg Gly Leu Tyr Gly Leu Asn Ala Ser Asn Thr His Arg
        1130                1135                1140

```
Ala Arg Gly Pro His Glu Thr His Arg Pro Arg Ala Val Ala Leu
    1145                1150                1155

Gly Leu Tyr Val Ala Leu Ile Leu Glu Gly Leu Asn Ala Ser Pro
    1160                1165                1170

Gly Leu Tyr Ser Glu Arg Ser Glu Arg Ala Leu Ala His Ile Ser
    1175                1180                1185

Ala Arg Gly Ala Ser Asn Gly Leu Ala Pro Arg Ala Gly Leu Asn
    1190                1195                1200

Gly Leu Asn Thr Arg Pro Val Ala Leu Leu Glu Ala Pro Arg Ala
    1205                1210                1215

Ala Ser Pro Thr Tyr Arg Ser Glu Arg Gly Leu Tyr Ala Arg Gly
    1220                1225                1230

Thr His Arg Val Ala Leu His Ile Ser Ala Ser Asn Val Ala Leu
    1235                1240                1245

His Ile Ser Leu Glu Ala Ala Leu Ala Pro Arg Ala Ala Leu Ala
    1250                1255                1260

Val Ala Leu Ala Leu Ala Pro Arg Ala Thr His Arg Pro His Glu
    1265                1270                1275

Pro Arg Ala Gly Leu Tyr Gly Leu Ala Gly Leu Asn Leu Glu Ala
    1280                1285                1290

Leu Glu Ala Pro His Glu Pro His Glu Ala Arg Gly Ser Glu Arg
    1295                1300                1305

Thr His Arg Met Glu Thr Pro Arg Ala Gly Leu Tyr Cys Tyr Ser
    1310                1315                1320

Ser Glu Arg Gly Leu Tyr Thr Tyr Arg Pro Arg Ala Ala Ser Asn
    1325                1330                1335

Met Glu Thr Ala Ser Pro Leu Glu Ala Ala Ser Pro Cys Tyr Ser
    1340                1345                1350

Leu Glu Ala Leu Glu Ala Pro Arg Ala Gly Leu Asn Gly Leu Ala
    1355                1360                1365

Thr Arg Pro Val Ala Leu Gly Leu Asn His Ile Ser Pro His Glu
    1370                1375                1380

Thr Tyr Arg Gly Leu Asn Gly Leu Ala Ala Leu Ala Ala Leu Ala
    1385                1390                1395

Pro Arg Ala Ala Leu Ala Gly Leu Asn Ser Glu Arg Ala Ser Pro
    1400                1405                1410

Val Ala Leu Ala Leu Ala Leu Glu Ala Leu Glu Ala Ala Arg Gly
    1415                1420                1425

Pro His Glu Val Ala Leu Ala Ser Asn Pro Arg Ala Ala Ser Pro
    1430                1435                1440

Thr His Arg Gly Leu Tyr Ala Arg Gly Val Ala Leu Leu Glu Ala
    1445                1450                1455

Pro His Glu Gly Leu Ala Cys Tyr Ser Leu Tyr Ser Leu Glu Ala
    1460                1465                1470

His Ile Ser Leu Tyr Ser Thr His Arg Gly Leu Tyr Thr Tyr Arg
    1475                1480                1485

Val Ala Leu Thr His Arg Val Ala Leu Ala Leu Ala His Ile Ser
    1490                1495                1500

Thr His Arg Gly Leu Tyr Gly Leu Asn His Ile Ser Ala Ser Pro
    1505                1510                1515

Leu Glu Ala Val Ala Leu Ile Leu Glu Pro Arg Ala Pro Arg Ala
    1520                1525                1530

Ala Ser Asn Gly Leu Tyr Thr Tyr Arg Pro His Glu Ala Arg Gly
```

Pro His Glu Ala Ser Pro Ser Glu Arg Thr Arg Pro Val Ala Leu
    1550               1555                1560

Ala Ser Asn Gly Leu Asn Pro His Glu Thr Tyr Arg Thr His Arg
    1565               1570                1575

Leu Glu Ala Ala Leu Ala Pro Arg Ala Met Glu Thr Gly Leu Tyr
    1580               1585                1590

Ala Ser Asn Gly Leu Tyr Ala Leu Ala Gly Leu Tyr Ala Arg Gly
    1595               1600                1605

Ala Arg Gly Ala Arg Gly Ala Leu Ala Leu Glu Ala
    1610               1615                1620

<210> SEQ ID NO 14
<211> LENGTH: 1620
<212> TYPE: DNA
<213> ORGANISM: Artificial Sequence
<220> FEATURE:
<223> OTHER INFORMATION: synthetic oligonucleotide

<400> SEQUENCE: 14

| | | | | | |
|---|---|---|---|---|---|
| atgaaaatgg | cgagcaatga | tgcgagcccg | agcgatggca | gcaccgcgaa | tctggtgccg | 60 |
| gaagtgaata | atgaagtgat | ggcgctggaa | ccggtggtgg | gcgcggcgat | tgcggcgccg | 120 |
| gtggcgggcc | agcagaatgt | gattgatccg | tggattcgca | ataattttgt | gcaggcgccg | 180 |
| ggcggcgaat | ttaccgtgag | cccgcgcaat | gcgccgggcg | aaattctgtg | gagcgcgccg | 240 |
| ctgggcccgg | atctgaatcc | gtatctgagc | catctggcgc | gcatgtataa | tggctatgcg | 300 |
| ggcggctttg | aagtgcaggt | gattctggcg | ggcaatgcgt | ttaccgcggg | caaaattatt | 360 |
| tttgcggcgg | tgccgccgaa | ttttccgacc | gaaggcctga | gcccgagcca | ggtgaccatg | 420 |
| tttccgcata | ttattgtgga | tgtgcgccag | ctggaaccgg | tgctgattcc | gctgccggat | 480 |
| gtgcgcaata | tttttatca | ttataatcag | agcaatgata | gcaccattaa | actgattgcg | 540 |
| atgctgtata | ccccgctgcg | cgcgaataat | gcgggcgatg | atgtgtttac | cgtgagctgc | 600 |
| cgcgtgctga | cccgtccgag | cccggatttt | gattttattt | ttctggtgcc | gccgaccgtg | 660 |
| gaaagccgta | ccaaaccgtt | taccgtgccg | gtgctgaccg | tggaagaaat | gaccaatagc | 720 |
| cgcttttccga | ttccgctgga | aaaactgttt | accggcccga | gcagcgcgtt | tgtggtgcag | 780 |
| ccgcagaatg | gcgctgcac | caccgatggc | gtgctgctgg | caccacccca | gctgagcccg | 840 |
| gtgaatattt | gcacctttcg | tggcgatgtg | acccatattc | gggcacccg | cacctatcgc | 900 |
| atgaatctgg | cgagccagaa | ttggaataat | tatgatccga | ccgaagaaat | tccggcgccg | 960 |
| ctgggcaccc | cggattttgt | gggcaaaatt | cagggcatgc | tgacccagac | caccaaaggc | 1020 |
| gatggcagca | cccgtggcca | taaagcgacc | gtgagcaccg | gcagcgtgga | ttttacccccg | 1080 |
| aaactgggca | gcgtgcagtt | tgcgaccgat | accgataatg | attttgaaac | cggccagaat | 1140 |
| acccgcttta | ccccggtggg | cgtgattcag | gatggcagca | gcgcgcatcg | caatgaaccg | 1200 |
| cagcagtggg | tgctgccgga | ttatagcggt | cgcaccgtgc | ataatgtgca | tctggcgccg | 1260 |
| gcggtggcgc | cgacctttcc | gggcgaacag | ctgctgtttt | ttcgcagcac | catgccgggc | 1320 |
| tgcagcggct | atccgaatat | ggatctggat | tgcctgctgc | cgcaggaatg | ggtgcagcat | 1380 |
| ttttatcagg | aagcggcgcc | ggcgcagagc | gatgtggcgc | tgctgcgctt | tgtgaatccg | 1440 |
| gataccggcc | gcgtgctgtt | tgaatgcaaa | ctgcataaaa | ccggctatgt | gaccgtggcg | 1500 |
| cataccggcc | agcatgatct | ggtgattccg | ccgaatggct | attttcgctt | tgatagctgg | 1560 | gtgaatcagt tttatacccct ggcgccgatg ggcaatggcg cgggccgccg tcgcgcgctg    1620

<210> SEQ ID NO 15
<211> LENGTH: 4
<212> TYPE: PRT
<213> ORGANISM: Artificial Sequence
<220> FEATURE:
<223> OTHER INFORMATION: synthetic peptide

<400> SEQUENCE: 15

Met Ser Glu Gln
1

<210> SEQ ID NO 16
<211> LENGTH: 6
<212> TYPE: PRT
<213> ORGANISM: Artificial Sequence
<220> FEATURE:
<223> OTHER INFORMATION: synthetic peptide

<400> SEQUENCE: 16

Glu Asn Leu Tyr Phe Gln
1               5

<210> SEQ ID NO 17
<211> LENGTH: 540
<212> TYPE: PRT
<213> ORGANISM: Artificial Sequence
<220> FEATURE:
<223> OTHER INFORMATION: peptide

<400> SEQUENCE: 17

Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Val Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

```
Lys Pro Phe Thr Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
            245                 250                 255

Phe Val Val Gln Pro Gln Asn Gly Arg Cys Thr Thr Asp Gly Val Leu
        260                 265                 270

Leu Gly Thr Thr Gln Leu Ser Pro Val Asn Ile Cys Thr Phe Arg Gly
    275                 280                 285

Asp Val Thr His Ile Pro Gly Thr Arg Thr Tyr Arg Met Asn Leu Ala
290                 295                 300

Ser Gln Asn Trp Asn Asn Tyr Asp Pro Thr Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Gly Asp Gly Ser Thr Arg Gly His Lys Ala Thr Val Ser
            340                 345                 350

Thr Gly Ser Val Asp Phe Thr Pro Lys Leu Gly Ser Val Gln Phe Ala
        355                 360                 365

Thr Asp Thr Asp Asn Asp Phe Glu Thr Gly Gln Asn Thr Arg Phe Thr
    370                 375                 380

Pro Val Gly Val Ile Gln Asp Gly Ser Ser Ala His Arg Asn Glu Pro
385                 390                 395                 400

Gln Gln Trp Val Leu Pro Asp Tyr Ser Gly Arg Thr Val His Asn Val
                405                 410                 415

His Leu Ala Pro Ala Val Ala Pro Thr Phe Pro Gly Glu Gln Ile Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Thr Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Ala Gly Arg Arg Arg Ala Leu
    530                 535                 540

<210> SEQ ID NO 18
<211> LENGTH: 26
<212> TYPE: PRT
<213> ORGANISM: Artificial Sequence
<220> FEATURE:
<223> OTHER INFORMATION: peptide

<400> SEQUENCE: 18

Met Lys Met Ala Ser Asn Asp Ala Ser Pro Ser Asp Gly Ser Thr Ala
1               5                   10                  15

Asn Leu Val Pro Glu Val Asn Asn Glu Val
            20                  25
```